US012780806B2

(12) United States Patent
Shi et al.

(10) Patent No.: US 12,780,806 B2
(45) Date of Patent: Nov. 3, 2026

(54) XANTHINE OXIDASE INHIBITOR

(71) Applicant: JIANGSU ATOM BIOSCIENCE AND PHARMACEUTICAL CO., LTD., Suzhou (CN)

(72) Inventors: Dongfang Shi, Fremont, CA (US); Changjin Fu, Suzhou (CN); Yan Yang, Suzhou (CN)

(73) Assignee: JIANGSU ATOM BIOSCIENCE AND PHARMACEUTICAL CO., LTD., Suzhou (CN)

( * ) Notice: Subject to any disclaimer, the term of this patent is extended or adjusted under 35 U.S.C. 154(b) by 371 days.

(21) Appl. No.: 18/557,919

(22) PCT Filed: Apr. 28, 2022

(86) PCT No.: PCT/CN2022/089979

§ 371 (c)(1),
(2) Date: Oct. 27, 2023

(87) PCT Pub. No.: WO2022/233264

PCT Pub. Date: Nov. 10, 2022

(65) Prior Publication Data

US 2024/0262808 A1 Aug. 8, 2024

(30) Foreign Application Priority Data

May 7, 2021 (CN) ......................... 202110493446.2

(51) Int. Cl.

| | |
|---|---|
| ***C07D 403/04*** | (2006.01) |
| ***A61K 31/416*** | (2006.01) |
| ***A61K 31/4192*** | (2006.01) |
| ***A61K 31/4439*** | (2006.01) |
| ***A61P 19/06*** | (2006.01) |
| ***C07D 231/56*** | (2006.01) |
| ***C07D 401/04*** | (2006.01) |
| ***C07D 405/14*** | (2006.01) |
| ***C07D 409/04*** | (2006.01) |

(52) U.S. Cl.

CPC .......... *C07D 403/04* (2013.01); *A61K 31/416* (2013.01); *A61K 31/4192* (2013.01); *A61K 31/4439* (2013.01); *A61P 19/06* (2018.01); *C07D 231/56* (2013.01); *C07D 401/04* (2013.01); *C07D 405/14* (2013.01); *C07D 409/04* (2013.01)

(58) Field of Classification Search

None

See application file for complete search history.

(56) References Cited

PUBLICATIONS

American Chemical Society. Chemical Abstract Service. RN 2850337-80-1. Entered into STN: Nov. 6, 2022. (Year: 2022).*

* cited by examiner

*Primary Examiner* — John S Kenyon

(74) *Attorney, Agent, or Firm* — CBM PATENT CONSULTING, LLC

(57) ABSTRACT

It discloses a compound shown in general formula (I) or a pharmaceutically acceptable salt thereof and a method for preparation of the compound; the compound is a xanthine oxidase inhibitor with xanthine oxidase inhibiting activity; the compound has an excellent xanthine oxidase inhibitory activity and has potential application value in anti-gout drugs, anti-hyperuricemia drugs, etc.

8 Claims, No Drawings

XANTHINE OXIDASE INHIBITOR

TECHNICAL FIELD

The invention belongs to the technical field of medicine, and in particular relates to a compound with inhibiting effect on xanthine oxidase.

BACKGROUND OF THE INVENTION

Gout (gout) is a disease caused by long-term purine metabolism disorder in the human body, resulting in excessive production of uric acid and/or poor excretion of uric acid, continuous increase of blood uric acid (sUA) level, crystallization of sodium urate and deposition in the body. Its main manifestations are recurrent joint redness, swelling, fever, pain and dysfunction, and even joint malformation, nephrolithiasis and uric acid nephropathy.

In recent years, with the continuous improvement of living standards, people's diet has also changed, and the number of gout patients has increased significantly. Gout, which has become the second largest metabolic disease after diabetes, has been listed by the United Nations as one of the twenty biggest diseases of the 21st century. According to the US National Health and Nutrition Examination Survey, the prevalence of gout among U.S. adults in 2007-2008 was 3.9% (about 8.3 million individuals). (Zhu Y, Pandya B J, Choi H K. Prevalence of Gout and Hyperuricemia in the US General Population: The National Health and Nutrition Examination Survey 2007-2008[J]. Arthritis Rheum, 2011, 63(10): 3136-3141); Meta-analysis showed that the overall prevalence of hyperuricemia in China was 13.3% and that of gout was 1.1% (Liu R, Han C, Wu D, et al. Prevalence of hyperuricemia and gout in mainland China from 2000 to 2014: A systematic review and meta-analysis[J]. Biomed Research International, 2015: 1-12). In the past few decades, the incidence of gout has increased due to the prevalence of co-morbiditions that promote hyperuricemia (e.g., hypertension, obesity, metabolic syndrome, type 2 diabetes, chronic kidney disease) (Khanna D, Fitzgerald J D, Khanna P P, et al. American College of Rheumatology Guidelines for Management of Gout. Part 1: Systematic Nonpharmacologic and Pharmacologic Therapeutic Approaches to Hyperuricemia [J]. Arthritis Care & Research, 2012, 64(10): 1432-1446).

The treatment of gout includes two aspects: drug therapy and non-drug therapy. Non-drug therapy is an important part of gout treatment, including diet control and lifestyle adjustments (e.g. weight loss, physical exercise). Drug therapy for chronic gout usually focuses on reducing sUA levels (Qaseem A, Harris R, Foricea M A. Clinical Guidelines Committee of the ACP. Management of Acute and Recurrent Gout: A Clinical Practice Guideline from the American College of Physicians[J]. Annals of Internal Medicine, 2017, 166(1): 58-68). At present, there are three main types of drugs for the treatment of gout: anti-acute gout arthritis drugs, drugs that decrease uric acid formation, and drugs that increase uric acid renal excretion.

Anti-acute gout arthritis drugs such as colchicine, non-steroidal anti-inflammatory drugs (NSAIDS), corticotropins, glucocorticoids, etc., are mainly used to treat acute gout arthritis and can relieve patients' temporary pain. Colchicine is often accompanied by diarrhea, vomiting, abdominal cramps and other common adverse reactions. NSAIDS can provide short-term pain relief, but most NSAIDS are associated with severe gastrointestinal reactions. Corticotropins and glucocorticoids can inhibit non-infectious inflammation, reduce congestion and edema, inhibit inflammatory cell movement, and reduce autoimmune levels. They are used to treat patients with severe acute gout accompanied by systemic symptoms, but these drugs have a very strong rebound effect.

Drugs that increase uric acid renal excretion mainly include probenecid, Lesinurad and benzbromarone. These drugs can inhibit the reabsorption of uric acid by the renal tubules and act on urate transporters in the renal proximal tubules, thereby inhibiting the reabsorption of uric acid and increasing its excretion, thereby reducing the uric acid concentration in the body. In US guideline, probenecid is the first choice of uricosuric drugs in monotherapy for lowering uric acid, but its use is limited due to its multiple significant interactions with some commonly used drugs (such as non-steroidal anti-inflammatory drugs, β-lactam drugs, heparin, etc.). Lesinurad, a new urate transporter 1 (URAT1) inhibitor approved by the FDA in 2015, has a black box warning in the package insert that it may cause acute kidney failure and cardiovascular disease risk (possible death). For these reasons, Lesinurad is not recommended for patients with heart failure who have uncontrolled hypertension, unstable angina pectoris, recent myocardial infarction, or NYHA in classes III to IV. It is prohibited in patients with end-stage renal disease, kidney transplantation or dialysis (Bardin T, Richette P. Novel uricosurics). Rheumatology, 2018, 57(suppl.1): i42-i46. Benzbromarone is an effective uricosuric drug that has been approved in many countries, but not in the United States. Benzbromarone was withdrawn from some European countries in 2003 due to severe liver toxicity, but it is still used to treat gout in some countries. Up to now, in Japan, Australia, New Zealand and some European countries, benzbromarone has been recognized as an effective drug for gout patients who are intolerant to allopurinol as a result of treatment with cyclosporine after organ transplantation. Due to ethnic differences in liver related adverse events associated with benzbromarone, the guideline for the diagnosis and management of hyperuricemia and gout in China (2019) recommend benzbromarone as a first-line uric acid-lowering drug.

In human metabolism, xanthine oxidase catalyzes the last two steps of purine metabolism, the oxidation of hypoxanthine to xanthine and the oxidation of xanthine to uric acid, and a sustained increase uric acid concentration in the blood can lead to the occurrence of many diseases, including gout. Therefore, xanthine oxidase is closely related to the occurrence of gout. Inhibiting xanthine oxidase can block the pathway of purine metabolism into uric acid in human body, effectively reduce sUA level, and prevent and treat the occurrence and development of gout and hyperuricemia. Compounds with xanthine oxidase inhibitory activity that have been publicly reported include a class of compounds disclosed by CN102574839A with the structure shown in formula (G), and a class of compounds disclosed by the applicant's earlier patent CN103980267A with the structure shown in formula (F), etc. At present, the drugs that have been used in the market mainly include allopurinol and febuxostat.

(F)

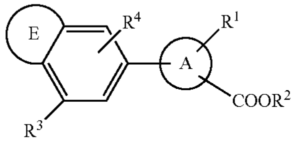

-continued (G)

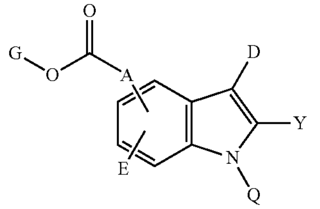

Allopurinol, an analogue of hypoxanthine, is recommended as a first-line drug for treatment of chronic gout. However, the curative effect of allopurinol is not satisfactory, and studies have shown that even if allopurinol is used at maximum doses, less than 50% of subjects reach the treatment endpoint (Robert M, Douglas C A, Scott B. Less than half of patients treated with high-Dose allopurinol reach serum uric acid target[J]. ACR/ARHP Annual Meeting, 2017, Abstract Number: 1120). It can also cause rashes and other rare but fatal side effects, including Stevens-Johnson syndrome, toxic epidermal necrolysis, with a fatality rate of about 10% to 30% (Bocquet H, Bagot M, Roujeau J C. Drug-induced pseudolymphoma and drug hypersensitivity syndrome (drug rash with eosinophilia and systemic symptoms: DRESS[J]. Seminars in Cutaneous Medicine and Surgery, 1996, 15(4): 250-257). Other side effects of allopurinol include stomach discomfort, nausea, abdominal pain, diarrhea, leukopenia and thrombocytopenia, headache, fever, loss of appetite, weight loss, painful urination, hematuria, itching and drowsiness.

Febuxostat is a new generation of XOI that inhibits both the oxidation and reducing states of xanthine oxidase, but its cardiovascular toxicity (such as the risk of sudden death) led the U.S. Food and Drug Administration to require a black box risk warning on its package insert and change prescribing information from first-line to second-line in 2019. In March 2018, the New England Journal of Medicine published the results of a study of 6,190 patients with gout: we found that after an average of 32 months of treatment, the overall risk of adverse cardiovascular events was similar in the febuxostat and allopurinol groups (HR 1.03, 95% CI, 0.87-1.23), but all-cause mortality and cardiovascular mortality were higher in the febuxostat group than in the allopurinol group. Patients in the Febuxostat group had a 34% increase in cardiovascular mortality (HR 1.34, 95% CI, 1.03-1.73) and a 22% increase in all-cause mortality (HR 1.22, 95% CI, 1.01-1.47). Sudden cardiac death was the most common cause of cardiovascular death, with 83 cases (2.7%) in the febuxostat group, 56 cases (1.8%) in allopurinol group (William B, Kenneth G, Michael A, et al. Cardiovascular safety of febuxostat or allopurinol in patients with gout[J]. The New England Journal of Medicine, 2018, 378:1200-1210). In addition, febuxostat may also cause serious gastrointestinal side effects, kidney side effects, liver function abnormalities, etc.

So far, xanthine oxidase inhibitors, including allopurinol and febuxostat, have a large risk of sudden death, as well as very serious renal, liver, gastrointestinal and other toxicity problems, which greatly limit the use of this class of drugs, resulting in relatively few inhibitor drugs that target xanthine oxidase.

SUMMARY OF THE INVENTION

One object of the present invention is to provide a compound with xanthine oxidase inhibiting activity on the basis of the prior art.

Another object of the invention is to provide method for preparation of the said compound and its use in the field of medicine.

The technical solution of the invention is provided as follows:

A compound shown in general formula (I) or a pharmaceutically acceptable salt thereof, (I)

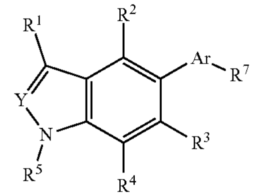

wherein,

Y is N or C—$R^6$;

$R^1$ is cyano, nitro or halogen;

$R^2$, $R^3$, or $R^4$ is independently hydrogen, deuterium, cyano, halogen, hydroxyl, amino, nitro, $C_{1-6}$ alkyl, substituted $C_{1-6}$ alkyl, $C_{1-6}$ alkoxy, or substituted $C_{1-6}$ alkoxy, respectively; the substituents of the groups involved in $R^2$, $R^3$ or $R^4$ are independently selected from one or more of the group consisting of deuterium, hydroxyl, cyano, halogen, $C_{1-4}$ alkyl and $C_{1-4}$ alkoxy;

$R^5$ is $C_{1-6}$ alkyl, substituted $C_{1-6}$ alkyl, $C_{3-6}$ cycloalkyl, substituted $C_{3-6}$ cycloalkyl, $C_{3-6}$ heterocycloalkyl or substituted $C_{3-6}$ heterocycloalkyl, the substituents of each group involved in $R^5$ are selected from one or more of the group consisting of deuterium, cyano, nitro, halogen, $C_{1-6}$ alkyl, $C_{1-6}$ alkoxy, $C_{3-6}$ cycloalkyl and $C_{3-6}$ heterocycloalkyl;

$R^6$ is hydrogen, deuterium, halogen, cyano, $C_{1-6}$ alkyl, substituted $C_{1-6}$ alkyl, $C_{1-6}$ alkoxy, substituted $C_{1-6}$ alkoxy, $C_{3-6}$ cycloalkyl or substituted $C_{3-6}$ cycloalkyl, the substituents of each group involved in $R^6$ are selected from one or more of the group consisting of deuterium, cyano, nitro, halogen, $C_{1-4}$ alkyl, $C_{1-4}$ alkoxy, $C_{1-4}$ alkylthio and $C_{3-6}$ cycloalkyl;

Ar is a non-substituted or substituted for the following groups: 1,2,3-triazolyl, pyrazolyl, pyridinyl, or thiophenyl, wherein the substituents of the groups involved in Ar are selected from one or more of the group consisting of the deuterium, halogen, and $C_{1-3}$ alkyl; and when Y is C—$R^6$, Ar is only a non-substituted or substituted 1,2,3-triazolyl;

$R^7$ is a carboxyl or $C_{2-6}$ ester group.

In one preferred embodiment, Ar is substituted or non-substituted for the following groups:

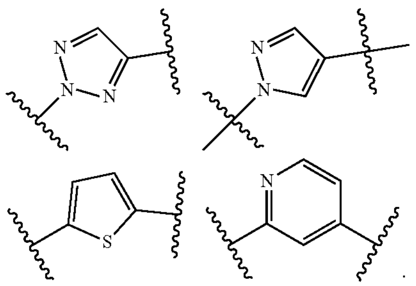

In one preferred embodiment, Ar is substituted or non-substituted group of the following, and "*" is the binding site of Ar with benzene ring:

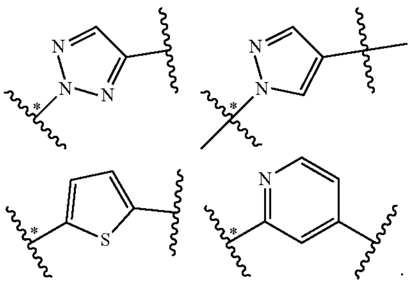

In one preferred embodiment, the substituents of each group involved in Ar are selected from one or more of the group consisting of deuterium, halogen and $C_{1-3}$ alkyl.

In one preferred embodiment, $R^2$, $R^3$ or $R^4$ is independently hydrogen, deuterium, cyano or halogen, respectively.

In one preferred embodiment, $R^5$ is $C_{3-6}$ alkyl, substituted $C_{1-6}$ alkyl, $C_{3-6}$ cycloalkyl, substituted $C_{3-6}$ cycloalkyl, $C_{3-6}$ heterocycloalkyl or substituted $C_{3-6}$ heterocycloalkyl; the substituents of the groups involved in $R^5$ are selected from one or more of the group consisting of deuterium, cyano, nitro, halogen, $C_{1-5}$ alkyl, $C_{1-5}$ alkoxy and $C_{3-6}$ cycloalkyl. In one preferred embodiment, $R^5$ is $C_{3-6}$ alkyl, substituted $C_{1-6}$ alkyl, $C_{3-6}$ cycloalkyl, substituted $C_{3-6}$ cycloalkyl, tetrahydrofuran, substituted tetrahydrofuran, tetrahydrothiophene, substituted tetrahydrothiophene, tetrahydropyrrole or substituted tetrahydropyrrole; the substituents of the groups involved in $R^5$ are selected from one or more of the group consisting of deuterium, cyano, nitro, halogen, $C_{1-5}$ alkyl, $C_{1-5}$ alkoxy and $C_{3-6}$ cycloalkyl.

In one more preferred embodiment, $R^5$ is isopropyl, n-butyl, isobutyl, cyclopropyl, cyclobutyl, cyclopropyl methyl, tetrahydrofuran, tetrahydrothiophene, or tetrahydropyrrole.

In one preferred embodiment, $R^6$ is hydrogen, deuterium, halogen, cyano or $C_{1-5}$ alkyl.

In one preferred embodiment, the compound of the invention may be selected from the group consisting of the following:

7

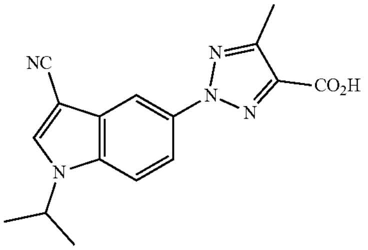

14

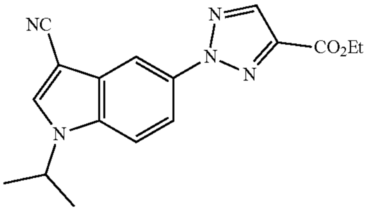

-continued

15

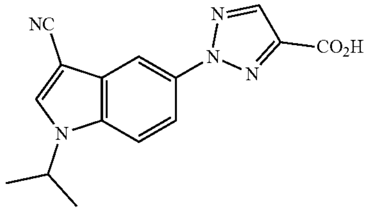

24

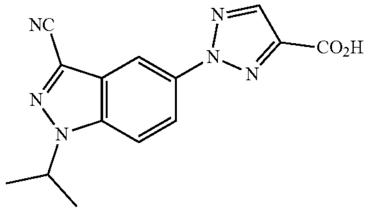

28

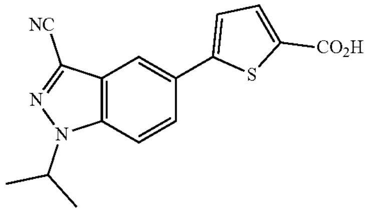

32

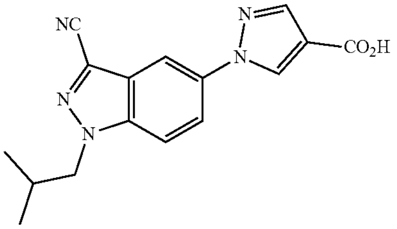

35

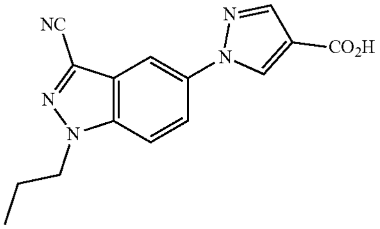

38

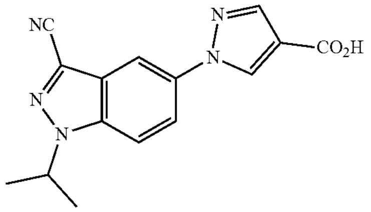

41

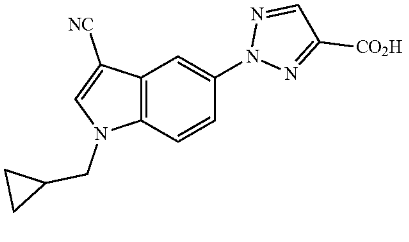

-continued

44

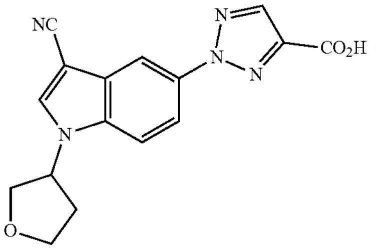

47

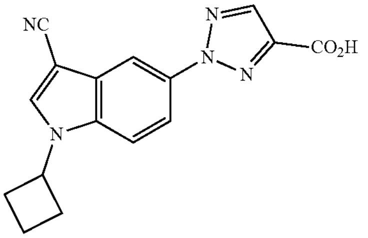

50

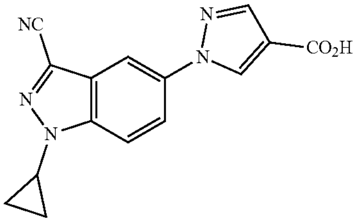

54

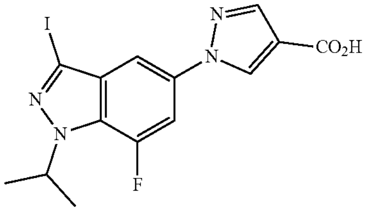

55

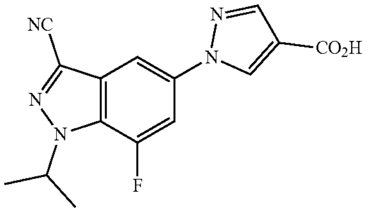

57

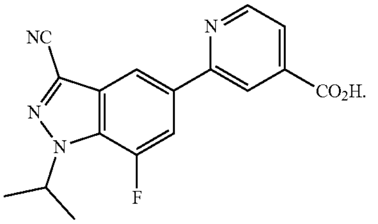

The invention also includes a pharmaceutical composition consisting of the compound or pharmaceutically acceptable salt thereof in the application as the active substance, in combination with pharmaceutically acceptable excipients.

The compound or pharmaceutically acceptable salts thereof can be used in the preparation of xanthine oxidase inhibitor drugs, in particular in the preparation of anti-gout drugs or anti-hyperuricemia drugs.

Each group indicated in the invention, unless otherwise expressly defined, has the following meanings:

"H", i.e. hydrogen, refers to Protium (1H), which is the main stable isotope of the element hydrogen.

"D", i.e. "deuterium", refers to a stable form isotope of hydrogen, also known as heavy hydrogen, whose element symbol is D.

"Halogen" refers to an atom of fluorine, chlorine, bromine or iodine.

"Hydroxyl" refers to —OH group.

"Amino" refers to —$NH_2$ group.

"Alkyl" refers to a saturated alkyl group containing 1-10 carbon atoms, including straight and branched chain groups (the range of numbers referred to in this application, e.g. "1-10", refers to the group, which is an alkyl group and may contain 1 carbon atom, 2 carbon atoms, 3 carbon atoms, etc., up to including 10 carbon atoms). Alkyl groups with 1-4 carbon atoms are called lower alkyl groups. When the lower alkyl group has no substituent, it is said to be an unsubstituted lower alkyl group. Alkyl can be $C_{1-6}$ alkyl, $C_{1-5}$ alkyl, $C_{1-4}$ alkyl, $C_{1-3}$ alkyl, $C_{1-2}$ alkyl, $C_{2-3}$ alkyl, $C_{2-4}$ alkyl, etc. Specific alkyl groups include, but are not limited to, methyl, ethyl, propyl, 2-propyl, n-butyl, isobutyl, or tert-butyl. Alkyl groups can be substituted or unsubstituted.

"Cycloalkyl" refers to a saturated cyclic aliphatic group containing 3 to 10 carbon atoms, and the range of numbers referred to in this application, such as "3 to 10", refers to the group, which is at this time a cycloalkyl group and may contain 3 carbon atoms, 4 carbon atoms, 5 carbon atoms, etc., until 10 carbon atoms are included as ring atoms. Cycloalkyl can be $C_{3-8}$ cycloalkyl, $C_{3-6}$ cycloalkyl, $C_{3-5}$ cycloalkyl, $C_{3-4}$ cycloalkyl, $C_{3-9}$ cycloalkyl, $C_{4-6}$ cycloalkyl, etc. Specific alkyl groups include but are not limited to cyclopropyl, cyclobutyl, cycloamyl, cyclohexyl, cycloheptyl, cyclooctyl, etc. Cycloalkyl groups can be substituted or unsubstituted.

"Heterocycloalkyl" refers to a saturated ring group containing 3-10 ring atoms, and its ring atoms contain one or more heteroatoms selected from N, O, and S. The range of numbers referred to in this application, such as "3-6", refers to the group, which is at this time a heterocycloalkyl group and may contain 3 carbon atoms, 4 carbon atoms, 5 carbon atoms, etc., up to including 6 carbon atoms as ring atoms. Heterocycloalkyl can be $C_{3-8}$ heterocycloalkyl, $C_{3-6}$ heterocycloalkyl, $C_{3-5}$ heterocycloalkyl, $C_{3-4}$ heterocycloalkyl, $C_{3-9}$ heterocycloalkyl, $C_{4-6}$ heterocycloalkyl, etc. Specific alkyl groups include, but are not limited to, tetrahydrofuran, tetrahydropyrrole, tetrahydrothiophene, 1,4-dioxane, oxaspiro[3,3]heptanyl, oxaspiro[4,4]nonyl, oxaspiro[5,5]undecyl, oxaspiro[6,6]tridecyl, oxabicyclo[1,1,1]pentyl, oxabicyclo[2,2,2]octyl, oxabicyclo[2,2][3,2,1]octyl, azaspiro[3,3]heptanyl, azaspiro[4,4]nonanyl, azaspiro[5,5]undecyl, azaspiro[6,6]tridecyl, azabicyclo[1,1,1]pentyl, azabicyclo[2,2,2]octyl or azabicyclo[3,2,1]octyl, etc. Heterocycloalkyl can be substituted or unsubstituted.

"Haloalkyl" refers to an alkyl group in which one, two, three, four or more hydrogens of the alkyl group are substituted by one or more halogens; Among them, alkyl can be $C_{1-6}$ alkyl, $C_{1-5}$ alkyl, $C_{1-4}$ alkyl, $C_{1-3}$ alkyl, $C_{1-2}$ alkyl, $C_{2-3}$ alkyl, $C_{2-4}$ alkyl, etc. It includes, but is not limited to, monofluoromethyl, difluoromethyl, trifluoromethyl, monochloromethyl, dichloromethyl, trichloromethyl, monobromomethyl, monofluoroethyl, difluoroethyl, trifluoroethyl, etc.

"Alkoxy", denotes —O— (unsubstituted alkyl) and —O— (unsubstituted cycloalkyl) groups, and further denotes —O— (unsubstituted alkyl). Among them, alkyl can be $C_{1-6}$ alkyl, $C_{1-5}$ alkyl, $C_{1-4}$ alkyl, $C_{1-3}$ alkyl, $C_{1-2}$ alkyl, $C_{2-3}$ alkyl, $C_{2-4}$ alkyl, etc. Representative examples include, but are not limited to, methoxy, ethoxy, propoxy, cyclopropoxy, etc.

"Alkylthio", denotes —S— (unsubstituted alkyl) and —S— (unsubstituted cycloalkyl) groups, and further denotes —S— (unsubstituted alkyl). Among them, alkyl can be $C_{1-6}$ alkyl, $C_{1-5}$ alkyl, $C_{1-4}$ alkyl, $C_{1-3}$ alkyl, $C_{1-2}$ alkyl, $C_{2-3}$ alkyl, $C_{2-4}$ alkyl, etc. Representative examples include, but are not limited to, methyl thio, ethyl thio, propyl thio, cyclopropyl thio, etc.

"Cyano" refers to —CN group.

"Nitro" refers to —$NO_2$ group.

"Carboxyl" refers to —COOH group.

"1,2,3-triazolyl" refers to any one of

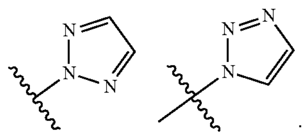 [SMILES: *n1nccn1 ; *n1ccnn1]

.

"Pyrazole," refers to any one of

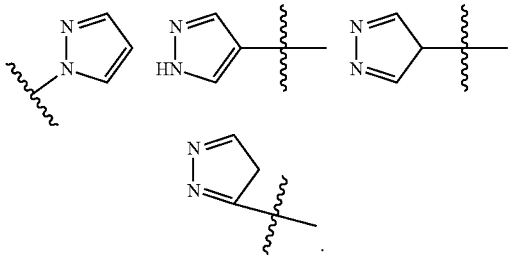

.

"Thiophene" refers to any one of

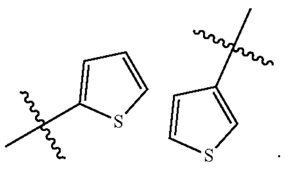

.

"Ester group" refers to "—C(═O)—O-alkyl" group, among which alkyl groups can be selected $C_{1-6}$ alkyl, $C_{1-5}$ alkyl, $C_{1-4}$ alkyl, $C_{1-3}$ alkyl, $C_{1-2}$ alkyl, $C_{2-3}$ alkyl, $C_{2-4}$ alkyl, etc. Representative examples include, but are not limited to, methyl formate, ethyl formate, n-propyl formate, isopropyl formate, etc. Substituted ester group refers to that in which the hydrogen in the ester group is replaced by a substituent, or multiple hydrogens in the ester group are replaced by the same or different substituents, respectively.

"Pharmaceutically acceptable salt" is a salt containing the compound of general formula (I) formed with organic or inorganic acid, indicating the salt that retain the biological availability and properties of the parent compound. Such salt includes, but is not limited to:

(1) salt formed with an acid, obtained by the reaction of the free base of the parent compound with inorganic or organic acid, such as (but not limited to) hydrochloric acid, hydrobromic acid, nitric acid, phosphoric acid, metaphosphoric acid, sulfuric acid, sulfite and perchloric acid, etc., organic acid, such as (but not limited to) acetic acid, propionic acid, acrylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, naphthalene-1-sulfonic acid, naphthalene-2-sulfonic acid, p-toluenesulfonic acid, salicylic acid, tartaric acid, citric acid, lactic acid, mandelic acid, succinic acid or malonic acid, etc.

(2) salt obtained by replacing the acid protons present in the parent compound with metal ion or obtained by coordination with organic base, metal ion, such as alkali metal ion, alkaline earth metal ion or aluminum ion, and organic base, such as ethanolamine, diethanolamine, triethanolamine, tromethamine, N-methylglucosamine, etc.

"Pharmaceutical composition" refers to one or more of the compounds described herein or pharmaceutically acceptable salt thereof and prodrug and mixture with other chemical components, such as pharmaceutically acceptable carriers and excipients. The pharmaceutical composition intends to facilitate the administration of a compound to an organism.

The invention is further directed to a pharmaceutical composition comprising any of the above compounds, pharmaceutically acceptable salts thereof or readily hydrolyzed prodrugs thereof and other pharmaceutical active ingredients.

The invention also includes any of the above-mentioned compounds, pharmaceutically acceptable salts thereof, which may be formulated into any clinically or pharmaceutically acceptable dosage form by processes known in the art. When used for oral administration, it can be prepared into conventional solid preparations, such as tablets, capsules, pills, granules, etc. It can also be prepared into oral liquid preparations, such as oral solution, oral suspension, syrups, etc. When preparing oral preparations, suitable fillers, adhesives, disintegrators, lubricants, etc., can be added. When used for parenteral administration, it can be prepared into injections, including injection, sterile powder for injection and concentrated solution for injection. When preparing injections, it can be produced by conventional methods in the existing pharmaceutical field, and when preparing injections, additional agents are not added, or appropriate additional agents can be added according to the nature of the drug.

The compounds provided by the invention have excellent xanthine oxidase inhibitory activity, and can also significantly reduce the serum uric acid level of hyperuricemia rat models, and have potential application value in the fields of anti-gout drugs and anti-hyperuricemia drugs. Because febuxostat has severe sudden cardiac death, severe renal toxicity and liver toxicity, the compounds provided by the invention may have certain advantages in reducing drug toxicity and have good drug development prospects.

DETAILED DESCRIPTION OF THE INVENTION

The detection method of the present invention is further illustrated by the following examples, but these examples do not constitute any limitation of the present invention.

Example 1: Synthesis of 2-(3-cyano-1-isopropyl-1H-indole-5-yl)-5-methyl-2H-1,2,3-triazole-4-formic acid (7)

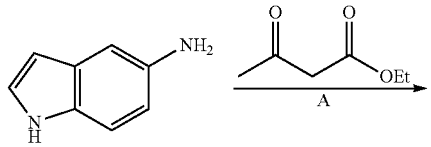

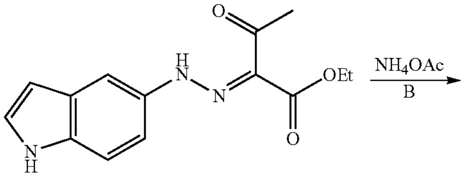

1

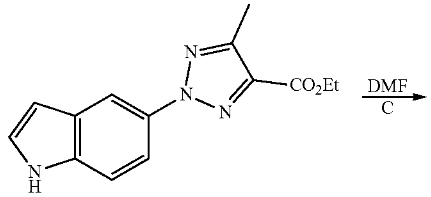

2

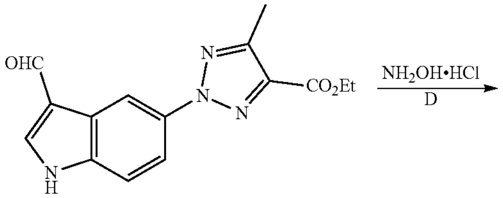

3

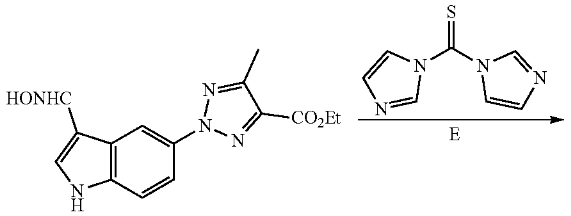

4

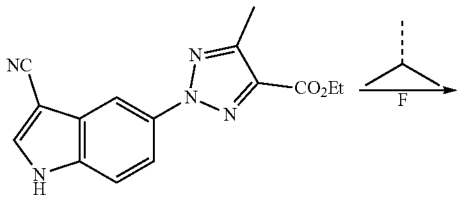

5

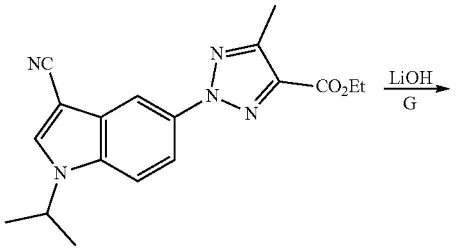

6

-continued

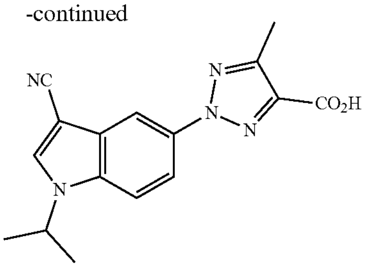

7

Step A: Under an ice water bath, a solution of sodium nitrite (3.13 g, 45.4 mmol) in water (20 mL) was added to a mixture containing 5-amino-indole (5.0 g, 37.8 mmol), water (80 mL), and 6 M hydrochloric acid (18.9 mL). After addition, stirring continued at this temperature for 30 minutes. Then, ethyl acetoacetate (10.8 g, 83.2 mmol) was added dropwise, and a solution of sodium acetate (93.1 g, 1.13 mol) in water (100 mL) was added to adjust the pH to be neutral. After addition, stirring continued at this temperature for 30 minutes. After filtering, filtrate was extracted with methylene chloride (300 mL×3), combined organic phase was washed with saturated salt water (200 mL), and dried over anhydrous sodium sulfate. The product was purified by column chromatography (200~300 mesh silica gel, elution with ethyl acetate:petroleum ether=1:10~2:3) to obtain ethyl 2-[2-(1H-indole-5-yl) hydrazino]-3-oxo-butyrate (1) (1.77 g). The yield was 14.3%.

Step B: the mixture containing compound 1 (1.50 g, 5.49 mmol), ammonium acetate (4.23 g, 54.9 mmol), copper chloride (1.62 g, 12.1 mmol), and ethanol (20 mL) was stirred under reflux overnight. After cooling to room temperature, pH was adjusted to 1~2 with 1 M hydrochloric acid. After filtering, filter cake was purified by column chromatography (200~300 mesh silica gel, elution with ethyl acetate:petroleum ether=1:10~1:2) to obtain ethyl 2-(1H-indole-5-yl)-5-methyl-2H-1,2,3-triazole-4-formate (2) (700 mg). The yield was 47.2%.

Step C: DMF (30.5 mg, 0.418 mmol) was added dropwise to a solution of oxalyl chloride (53.00 mg, 0.418 mmol) in dichloromethane (3 mL) under an ice water bath. After adding, the mixture was stirred continuously at this temperature for 0.5 hours. Compound 2 (100 mg, 0.370 mmol) was added and the resulting mixture was stirred under reflux for 1 hour. A solution of THF (8 mL) and amine acetate (1.80 g, 23.4 mmol) in water (8 mL) was added. After heating to 80° C. and stirring for 0.5 hours, and then cooling to room temperature, water (10 mL) was added, extraction was carried out with ethyl acetate (10 mL×2), the combined organic phase was washed with saturated salt water (20 mL), and dried over anhydrous sodium sulfate. A crude product (100 mg) of ethyl 2-(3-formyl-1H-indole-5-yl)-5-methyl-1,2,3-triazole-4-formate (3) was obtained by evaporation under reduced pressure. The compound was directly used in the next reaction without purification. MS (ESI, m/z): 299.2 $[M+H]^+$.

Step D: a mixture containing crude compound 3 (100 mg), hydroxylamine hydrochloride (26.5 mg, 0.381 mmol), and pyridine (3 mL) was stirred under reflux for 1 hour. After cooling to room temperature, water (10 mL) was added, extraction was carried out with ethyl acetate (10 mL×2), the combined organic phase was washed with saturated salt water (20 mL), and dried over anhydrous sodium sulfate. The product was purified by column chromatography (200~300 mesh silica gel, elution with ethyl acetate:petroleum ether=1:10~1:3), and ethyl 2-{3-[(hydroxyimino-amido)methyl]-1H-indole-5-yl}-5-methyl-2H-1,2,3-triazole-4-formate (4) (80 mg) was obtained. The total yield of steps C and D was 76.4%. MS (ESI, m/z): 314.2 $[M+H]^+$.

Step E: a mixture containing compounds 4 (80 mg, 0.255 mmol), THF (1 mL), and thiocarbonyl diimidazole (132 mg, 0.740 mmol) was stirred at room temperature for 1 hour. The solvent was evaporated under reduced pressure, and the product was purified by column chromatography (200~300 mesh silica gel, elution with ethyl acetate:petroleum ether=1:10~1:3) to obtain ethyl 2-(3-cyano-1H-indole-5-yl)-5-methyl-2H-1,2,3-triazole-4-formate (5) (75 mg). The yield was 99.6%. 1H NMR (DMSO-d6, 400 MHz) δ 12.52 (s, 1H), 8.40 (d, J=2.4 Hz, 1H), 8.19 (d, J=1.6 Hz, 1H), 8.00-7.97 (m, 1H), 7.74 (d, J=9.2 Hz, 1H), 4.39 (q, J=6.8 Hz, 2H), 2.56 (s, 3H), 1.36 (t, J=6.8 Hz, 3H).

Step F: A mixture containing compound 5 (75 mg, 0.254 mmol), isopropane iodide (95 mg, 0.559 mmol), cesium carbonate (166 mg, 0.508 mmol) and acetonitrile (3 mL) was stirred overnight at 80° C. After cooling to room temperature, water (15 mL) was added, the mixture was extracted with ethyl acetate (10 mL×3), and dried over anhydrous sodium sulfate. The product was purified by column chromatography (200~300 mesh silica gel, elution with ethyl acetate:petroleum ether=1:15~1:4) to obtain ethyl 2-(3-cyano-1-isopropyl-1H-indole-5-yl)-5-methyl-2H-1,2,3-triazole-4-formate (6) (70 mg). The yield was 81.7%.

Step G: a mixture containing compound 6 (60 mg, 0.178 mmol), hydrated lithium hydroxide (30 mg, 0.715 mmol), water (0.8 mL), and THF (3.2 mL) was stirred at room temperature overnight. pH was adjusted to 3~4 with 1 M hydrochloric acid. The solvent was evaporated under reduced pressure, and the product was purified by preparative HPLC to obtain 2-(3-cyano-1-isopropyl-1H-indole-5-yl)-5-methyl-2H-1,2,3-triazole-4-formic acid (7). $^1H$ NMR (DMSO-$d_6$, 400 MHz) δ 8.60 (s, 1H), 8.18 (d, J=2.0 Hz, 1H), 8.02-7.94 (m, 2H), 4.95-4.89 (m, 1H), 2.55 (s, 3H), 1.51 (d, J=6.8 Hz, 6H). MS (ESI, m/z): 310.2 $[M+H]^+$.

Example 2: Synthesis of ethyl 2-(3-cyano-1-isopropyl-1H-indole-5-yl)-2H-1,2,3-triazole-4-formate (14)

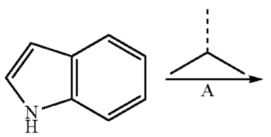

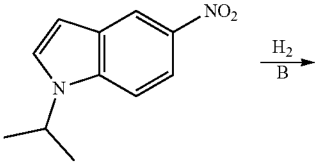

8

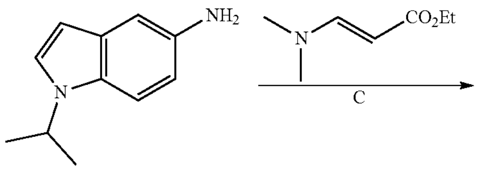

9

-continued

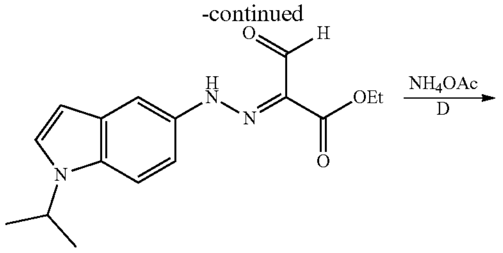

10

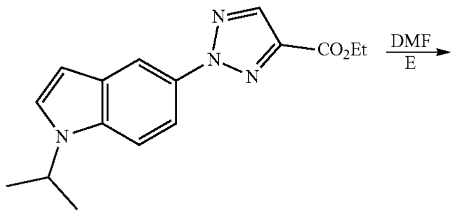

11

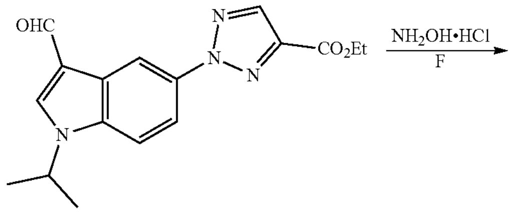

12

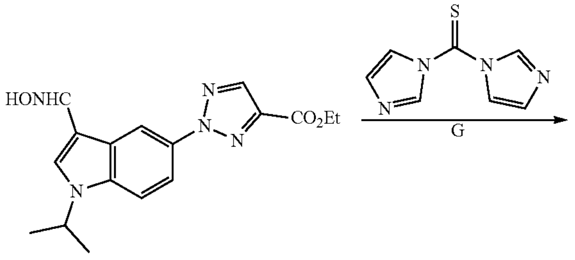

13

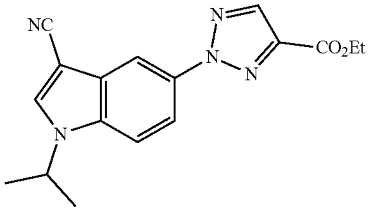

14

Step A: a mixture containing 5-nitro-1H-indole (30.0 g, 185 mmol), isopropane iodide (69.2 g, 407 mmol), cesium carbonate (121 g, 370 mmol) and acetonitrile (500 mL) was stirred at 80° C. overnight. After cooling to room temperature and filtering, the filter cake was rinsed with ethyl acetate. The solvent was evaporated under reduced pressure, and the product was purified by column chromatography (200~300 mesh silica gel, elution with ethyl acetate:petroleum ether=1:50~1:20) to obtain 1-isopropyl-5-nitro-1H-indole (8) (38.0 g). The yield was 100%.

Step B: 10% palladium carbon (4.0 g) was added to a solution of compound 8 (38.0 g, 185 mmol) in THF (50 mL) and methanol (200 mL). After addition, the resulting mixture was stirred at room temperature under hydrogen for 60 hours. Filtered through Celite, the filter cake was washed with ethyl acetate. 5-amino-1-isopropyl-1H-indole (9) (30.0 g) was obtained by solvent removal under reduced pressure. The yield was 93.1%.

Step C: Under an ice water bath, a solution of sodium nitrite (4.40 g, 63.8 mmol) in water (30 mL) was added dropwise to a mixture containing compound 9 (10 g, 57.4 mmol), water (200 mL) and 3 M hydrochloric acid (54 mL). After addition, stirring continued at this temperature for 1 hour. The mixture was then added dropwise to a mixture containing ethyl 3-(N,N-dimethylamino)acrylate (15.2 g, 106 mmol), sodium acetate (78.5 g, 957 mmol), and water (500 mL) under an ice water bath. After adding, stirring continued at this temperature for 30 minutes. The combined organic phase was extracted with methylene chloride (300 mL×3), washed with saturated salt water (200 mL), and dried over anhydrous sodium sulfate. After removing solvent by evaporation under reduced pressure, the product was purified by column chromatography (200~300 mesh silica gel, elution with ethyl acetate:petroleum ether=1:5) to give ethyl 2-[2-(1-isopropyl-1H-indole-5-1)hydrazino]-3-oxo-propanoate (10) (1.50 g). The yield was 8.67%.

Step D: a mixture containing compound 10 (1.50 g, 4.98 mmol), ammonium acetate (2.60 g, 33.7 mmol), copper chloride (1.26 g, 7.42 mmol), and ethanol (18 mL) was stirred overnight under reflux. After cooling to room temperature, water (80 mL) was added. The combined organic phase was extracted with ethyl acetate (40 mL×2), washed with saturated salt water (100 mL), and dried over anhydrous sodium sulfate. After removing solvent by evaporation under reduced pressure, the product was purified by column chromatography (200~300 mesh silica gel, elution with ethyl acetate:petroleum ether=1:7) to give ethyl 2-(1-isopropyl-1H-indole-5-yl)-2H-1,2,3-triazole-4-formate (11) (310 mg). The yield was 20.9%. $^1$H NMR ($CDCl_3$, 400 MHz) δ 8.38 (d, J=2.0 Hz, 1H), 8.23 (s, 1H), 8.00 (dd, J=2.0, 8.4 Hz, 1H), 7.44 (d, J=8.8 Hz, 1H), 7.31 (d, J=3.2 Hz, 1H), 6.61 (d, J=3.2 Hz, 1H), 4.75-4.68 (m, 1H), 4.48 (q, J=7.2 Hz, 2H), 1.56 (d, J=6.8 Hz, 6H), 1.45 (t, J=7.2 Hz, 3H). MS (ESI, m/z): 299.1 $[M+H]^+$.

The experimental operations of steps E, F, and G were successively referred to C, D, and E in Example 1 to obtain ethyl 2-(3-cyano-1-isopropyl-1H-indole-5-yl)-2H-1,2,3-triazole-4-formate (14). $^1$H NMR (DMSO-$d_6$, 400 MHz) δ 8.64 (s, 1H), 8.61 (s, 1H), 8.24 (d, J=2.0 Hz, 1H), 8.08-7.98 (m, 2H), 4.98-4.89 (m, 1H), 8.40 (q, J=7.2 Hz, 2H), 1.51 (d, J=6.4 Hz, 6H), 1.36 (t, J=7.2 Hz, 3H). MS (ESI, m/z): 324.2 $[M+H]^+$.

Example 3: Synthesis of 2-(3-cyano-1-isopropyl-1H-indole-5-yl)-2H-1,2,3-triazole-4-formic acid (15)

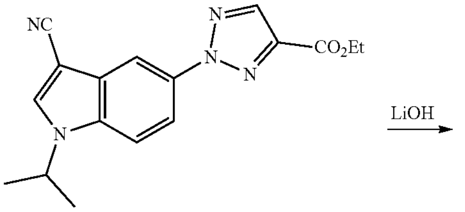

14

-continued

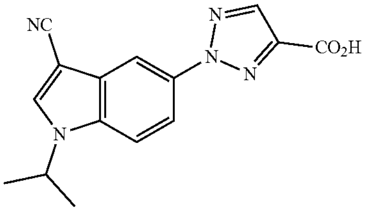

15

Using compound 14 as raw material, the experimental operations for the synthesis of compound 15 was referred to step G in Example 1. $^1$H NMR (DMSO-$d_6$, 400 MHz) δ 8.62 (s, 1H), 8.52 (s, 1H), 8.23 (s, 1H), 8.07-7.97 (m, 2H), 4.95-4.92 (m, 1H), 1.51 (d, J=5.6 Hz, 6H). MS (ESI, m/z): 296.1 $[M+H]^+$.

Example 4: Synthesis of 2-(3-cyano-1-isopropyl-1H-indazole-5-yl)-2H-1,2,3-triazole-4-formic acid (24)

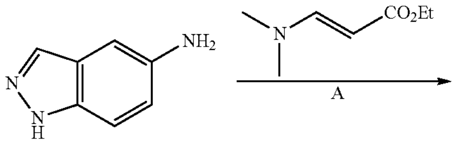

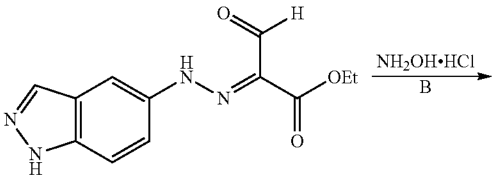

16

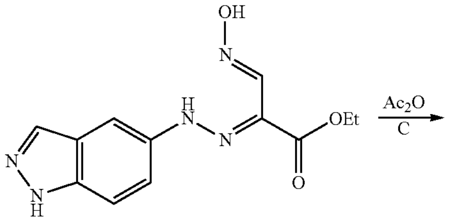

17

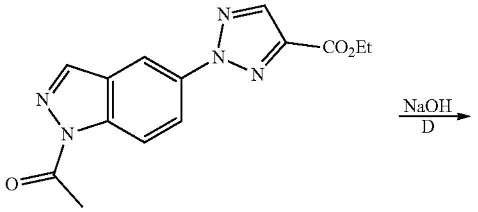

18

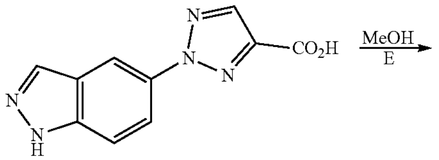

19

-continued

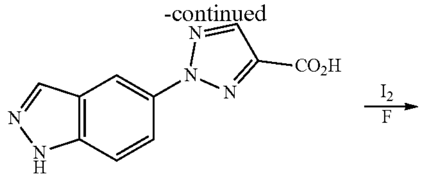

20

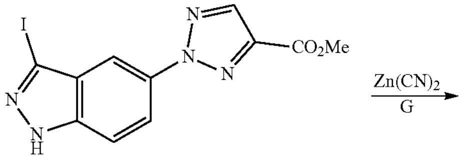

21

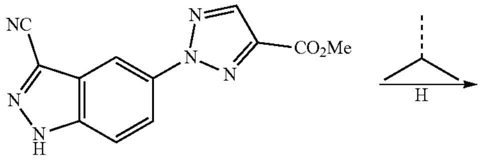

22

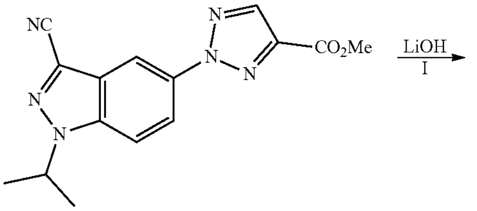

23

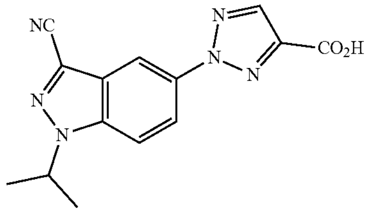

24

Step A: Under an ice water bath, a solution of sodium nitrite (4.35 g, 63.1 mmol) in water (50 mL) was added dropwise to 5-amino-1H-indazole (7.0 g, 52.6 mmol) in 3 M hydrochloric acid (53 mL). After adding, stirring continued at this temperature for 0.5 hours. The mixture was then added dropwise to a mixture containing ethyl 3-(N,N-dimethylamino) acrylate (15.1 g, 105 mmol), sodium acetate (77.6 g, 946 mmol), ethanol (40 mL), and water (400 mL) under an ice water bath. After adding, the resulting mixture was stirred at room temperature for 2 hours. After filtering and washing the cake with water, a crude product (20.0 g) of ethyl 2-[2-(1H-indozole-5-yl)hydrazino]-3-oxopropanoate (16) was obtained. The compound was directly used in the next reaction without purification.

Step B: hydroxylamine hydrochloride (8.01 g, 115 mmol) and sodium acetate (18.9 g, 231 mmol) were added to a mixture containing crude compound 16 (20.0 g), ethanol (100 mL) and water (50 mL). After adding, the resulting mixture was stirred at room temperature for 3 hours. Water (500 mL) was added, and the mixture was extracted with methylene chloride (200 mL×2), and dried over anhydrous sodium sulfate. The solvent was removed by evaporation under reduced pressure to obtain a crude product (14.5 g) of ethyl 2-[2-(1H-indozole-5-yl) hydrazino]-3-(hydroxyimino) propanoate (17). The compound was directly used in the next reaction without purification.

Step C: a mixture containing compound 17 crude (14.5 g), acetic acid (100 mL) and acetic anhydride (100 mL) was stirred at 60° C. for 4 hours. The product was purified by column chromatography (200~300 mesh silica gel, elution with ethyl acetate:petroleum ether=1:30~1:7) to give ethyl 2-(1-acetyl-1H-indazole-5-yl)-2H-1,2,3-triazole-4-formate (18) (1.80 g). The total yield of steps A, B and C was 11.4%. $^1$H NMR ($CDCl_3$, 400 MHz) δ 8.59-8.56 (m, 1H), 8.52 (d, J=1.6 Hz, 1H), 8.42-8.39 (m, 1H), 8.26 (s, 1H), 8.22 (s, 1H), 4.49 (q, J=7.2 Hz, 2H), 2.82 (s, 3H), 1.46 (t, J=7.2 Hz, 3H). MS (ESI, m/z): 300.2 $[M+H]^+$.

Step D: a mixture containing compound 18 (1.80 g, 6.01 mmol), methanol (20 mL), and sodium hydroxide (962 mg, 24.1 mmol) was stirred at room temperature overnight. pH was adjusted to 1~2 with 1 M hydrochloric acid. After filtration, the cake was washed with water and dried to obtain 2-(1H-indozole-5-yl)-2H-1,2,3-triazole-4-formic acid (19) (1.30 g). The yield was 94.3%.

Step E: sulfoxide chloride (3.37 g, 28.4 mmol) was added dropwise to a solution of compound 19 (1.30 g, 5.67 mmol) in methanol (20 mL) under an ice water bath. After addition, the resulting mixture was stirred overnight under reflux. The solvent was removed by evaporation under reduced pressure and then beaten with methylene chloride to obtain methyl 2-(1H-indozole-5-yl)-2H-1,2,3-triazole-4-formate (20) (1.30 g). The yield was 94.2%.

Step F: potassium carbonate (2.73 g, 19.7 mmol) and iodine (2.50 g, 9.87 mmol) were added to a solution of compound 20 (1.2 g, 4.93 mmol) in DMF (6 mL) under an ice water bath. After addition, the resulting mixture was stirred at room temperature overnight. Water (50 mL) was added and the excess iodine was quenched with sodium thiosulfate solution. The combined organic phase was extracted with ethyl acetate (50 mL×2), washed with saturated salt water (50 mL), and dried over anhydrous sodium sulfate. Methyl 2-(3-iodo-1H-indozole-5-yl)-2H-1,2,3-triazole-4-formate (21) (790 mg) was obtained by removing solvent by evaporation under reduced pressure. The yield was 43.4%. MS (ESI, m/z): 370.0 [M+H]+.

Step G: a mixture containing compounds 21 (780 mg, 2.11 mmol), DMF (10 mL), zinc cyanide (520 mg, 4.43 mmol), and tetrakis(triphenylphosphine)palladium (244 mg, 0.211 mmol) was stirred overnight under nitrogen at 120° C. Filtering was carried out to remove insolubles. Ethyl acetate (90 mL) was added, the combined organic phase was washed with saturated salt water (50 mL×3), and dried over anhydrous sodium sulfate. The solvent was evaporated under reduced pressure to obtain methyl 2-(3-cyano-1H-indazole-5-yl)-2H-1,2,3-triazole-4-formate (22) (400 mg). The yield was 70.7%. MS (ESI, m/z): 269.1 [M+H]+.

The experimental operations of steps H and I were referred to steps F and G in Example 1 to obtain 2-(3-cyano-1-isopropyl-1H-indazole-5-yl)-2H-1,2,3-triazole-4-formic acid (24). $^1$H NMR (DMSO-$d_6$, 400 MHz) δ 13.74 (s, 1H), 8.58 (s, 1H), 8.42 (s, 1H), 8.31-8.23 (m, 2H), 5.32-5.22 (m, 1H), 1.55 (d, J=6.4 Hz, 6H). MS (ESI, m/z): 296.9 $[M+H]^+$.

Example 5: Synthesis of 2-(3-cyano-1-isopropyl-1H-indazole-5-yl)thiophen-2-formic acid (28)

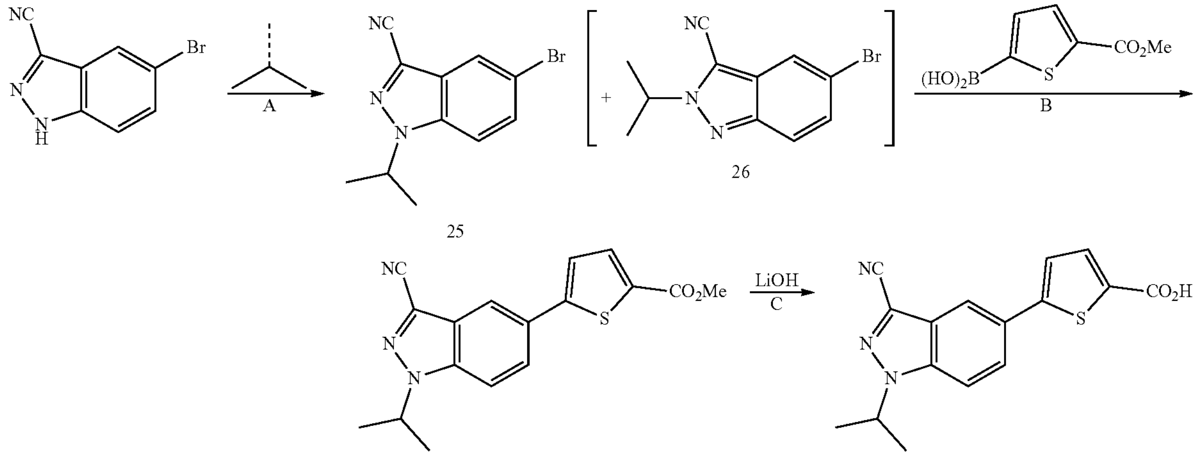

25 26 27 28

Step A: a mixture containing 5-bromo-1H-indazole-3-methyl nitrile (3.0 g, 13.5 mmol), isopropane iodide (9.19 g, 54.1 mmol), cesium carbonate (8.80 g, 27.0 mmol) and DMF (50 mL) was stirred at 80° C. for 1.5 hours. After cooling to room temperature and filtering to remove insolubles. Water (200 mL) was added, the mixture was extracted with ethyl acetate (80 mL×3), the combined organic phase was washed with water (50 mL×2) and saturated salt water (50 mL), and dried over anhydrous sodium sulfate. The solvents were evaporated under reduced pressure and the product was purified by column chromatography (200~300 mesh silica gel, elution with ethyl acetate:petroleum ether=1:50~1:30) to give 5-bromo-1-isopropyl-1H-indazole-3-methyl nitrile (25) (2.10 g) and 5-bromo-2-isopropyl-2H-indazole-3-methyl nitrile (26) (230 mg). The yields were 58.9% and 6.45%, respectively. Compound 25: $^1$H NMR ($CDCl_3$, 400 MHz) δ 7.95 (d, J=1.2 Hz, 1H), 7.55 (dd, J=1.2, 8.8 Hz, 1H), 7.45 (d, J=8.8 Hz, 1H), 4.93-4.87 (m, 1H), 1.61 (d, J=6.4 Hz, 6H). 化合物26: $^1$H NMR ($CDCl_3$, 400 MHz) δ 7.92 (d, J=1.2 Hz, 1H), 7.72 (d, J=8.8 Hz, 1H), 7.46-7.44 (m, 1H), 5.12-5.05 (m, 1H), 1.70 (d, J=6.4 Hz, 6H).

Step B: a mixture containing palladium acetate (16.6 mg, 0.0735 mmol), 2-dicyclohexylphosphino-2',6'-dimethoxybiphenyl (S-Phos) (60.3 mg, 0.147 mmol), and THF (2 mL) was stirred under nitrogen for 30 minutes, then a solution of compound 25 (200 mg, 0.735 mmol), thiophene-2-carboxylic acid methyl ester-5-boric acid (150 mg, 0.808 mmol) and potassium carbonate (508 mg, 3.67 mmol) in water (1 mL) was added. After addition, the resulting mixture was stirred overnight at 45° C. Water (20 mL) was added, the mixture was extracted with ethyl acetate (30 mL×2), the combined organic phase was washed with saturated salt water (15 mL), and dried over anhydrous sodium sulfate. The solvents were evaporated under reduced pressure and the product was purified by column chromatography (200~300 mesh silica gel, elution with ethyl acetate:petroleum ether=1:10) to give methyl 2-(3-cyano-1-isopropyl-1H-indazole-5-yl)-thiophen-2-format (27) (160 mg). The yield was 66.9%.

The experimental operations of Step C were referred to those of Step G in Example 1 to obtain 2-(3-cyano-1-isopropyl-1H-indazole-5-yl)-thiophen-2-formic acid (28). $^1$H NMR (DMSO-$d_6$, 400 MHz) δ 8.23 (s, 1H), 8.07 (d, J=8.8 Hz, 1H), 7.96-7.93 (m, 1H), 7.75 (s, 2H), 5.27-5.17 (m, 1H), 1.53 (d, J=6.4 Hz, 6H). MS (ESI, m/z): 312.2 $[M+H]^+$.

Example 6: Synthesis of 1-(3-cyano-1-isobutyl-1H-indazole-5-yl)-1H-pyrazole-4-formic acid (32)

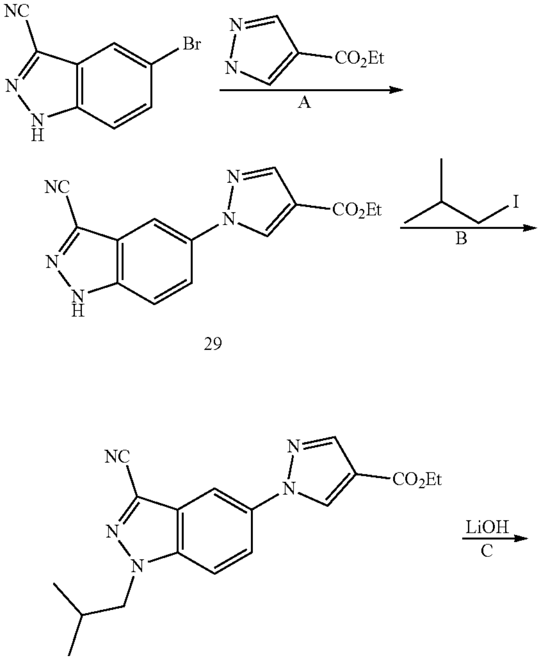

29 30

-continued

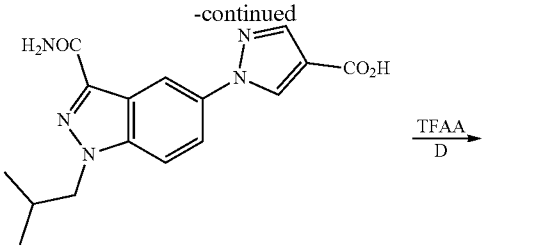

31

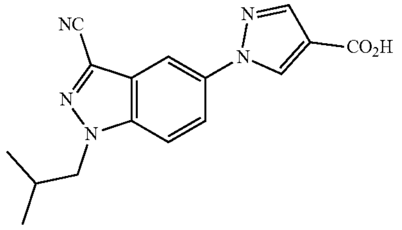

32

Step A: a mixture of ethyl 1H-pyrazole-4-formate (3.79 g, 27.0 mmol), 5-bromo-1H-indazole-3-methyl nitrile (3.0 g, 13.5 mmol), potassium carbonate (3.73 g, 27.0 mmol), cuprous iodide (2.57 g, 13.5 mmol), N,N'-dimethylethylene-diamine (1.19 g, 13.5 mmol) and DMF (30 mL) was stirred overnight under nitrogen at 110° C. After cooling to room temperature, adding ethyl acetate (300 mL) and filtering, the filtrate was washed with saturated salt water (300 mL×2), and dried over anhydrous sodium sulfate. The solvents were evaporated under reduced pressure and the product was purified by preparative HPLC to give ethyl 1-(3-cyano-1H-indazole-5-yl)-1H-pyrazole-4-formate (29) (600 mg). The yield was 15.8%.

Step B: a mixture containing compound 29 (300 mg, 1.07 mmol), isopropane iodide (328 mg, 1.78 mmol), cesium carbonate (581 mg, 1.78 mmol), and acetonitrile (3 mL) was stirred at 70° C. for 3 hours. After cooling to room temperature and filtering to remove insolubles, water (30 mL) was added, the mixture was extracted with ethyl acetate (30 mL×3), and dried over anhydrous sodium sulfate. The solvents were evaporated under reduced pressure and the product was purified by column chromatography (200~300 mesh silica gel, elution with ethyl acetate:petroleum ether=1:35~1:7) to give ethyl 1-(3-cyano-1-isobutyl-1H-indazole-5-yl)-1H-pyrazole-4-formate (30) (182 mg). The yield was 50.4%.

Step C: a mixture containing compound 30 (100 mg, 0.296 mmol), hydrated lithium hydroxide (49.8 mg, 1.19 mmol), water (0.6 mL), and THF (3.4 mL) at 40° C. was stirred overnight. The solvents were evaporated under reduced pressure, water (20 mL) was added, and the pH value was adjusted with 1 M hydrochloric acid to 1~2. The mixture was extracted with ethyl acetate (30 mL×2) and dried over anhydrous sodium sulfate. A crude product (129 mg) of 1-(3-aminoformyl-1-isobutyl-1H-indazole-5-yl)-1H-pyrazole-4-formic acid (31) was obtained by removing solvents by evaporation under reduced pressure. The compound was directly used in the next reaction without purification.

Step D: trifluoroacetic anhydride (792 mg, 3.77 mmol) and pyridine (1.03 g, 13.0 mmol) were added to a solution of crude compound 31 (120 mg) in dichloromethane (2 mL), and after addition, the resulting mixture was stirred at room temperature overnight. Ethyl acetate (100 mL) was added, the organic phase was washed with 1 M hydrochloric acid (50 mL×2), and dried over anhydrous sodium sulfate. The solvent was evaporated under reduced pressure and the product was purified by preparative HPLC to give 1-(3-cyano-1-isobutyl-1H-indazole-5-yl)-1H-pyrazole-4-formic acid (32). $^1$H NMR (DMSO-$d_6$, 400 MHz) δ 12.67 (s, 1H), 9.23 (s, 1H), 8.44 (s, 1H), 8.22-8.13 (m, 3H), 4.43 (d, J=7.2 Hz, 2H), 2.30-2.23 (m, 1H), 0.88 (d, J=6.4 Hz, 6H). MS (ESI, m/z): 310.3 $[M+H]^+$.

Example 7: Synthesis of 1-(3-cyano-1-propyl-1H-indazole-5-yl)-1H-pyrazole-4-formic acid (35)

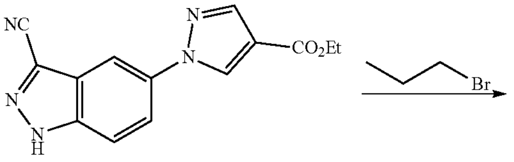

29

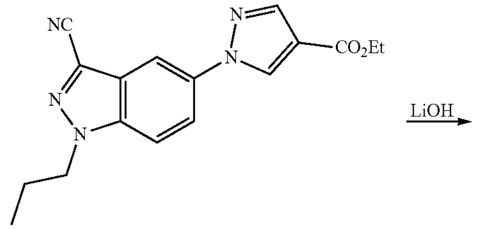

33

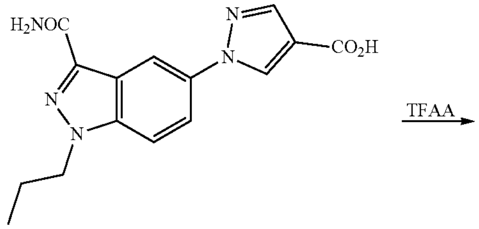

34

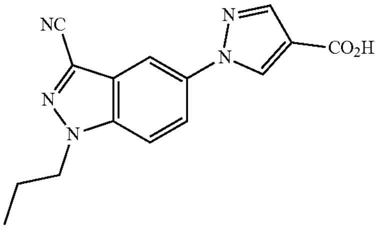

35

The experimental operations of compound 35 were referred to those in steps B, C, and D of Example 6, wherein iodoisobutane in step B of Example 6 was replaced by 1-bromopropane. $^1$H NMR (DMSO-$d_6$, 400 MHz) δ 9.22 (s, 1H), 8.43 (d, J=1.6 Hz, 1H), 8.22-8.13 (m, 3H), 4.56 (t, J=6.8 Hz, 2H), 1.95-1.88 (m, 2H), 0.85 (t, J=7.2 Hz, 3H). MS (ESI, m/z): 296.3 $[M+H]^+$.

Example 8: Synthesis of 1-(3-cyano-1-isopropyl-1H-indazole-5-yl)-1H-pyrazole-4-formic acid (38)

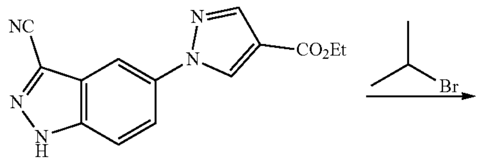

29

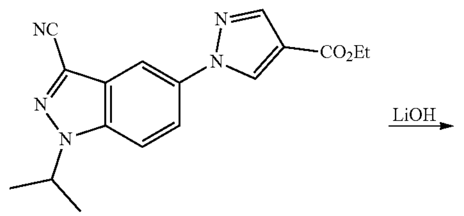

36

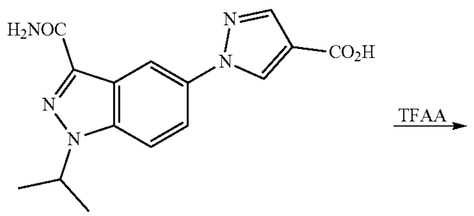

37

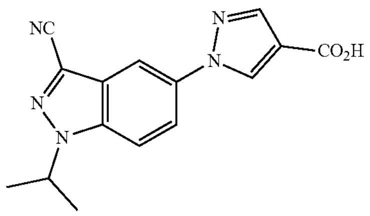

38

The experimental operations for the synthesis of compound 38 were referred to those in Steps B, C, and D of Example 6, wherein iodoisobutane in step B of example 6 was replaced by bromoisopropane. $^1H$ NMR (DMSO-$d_6$, 400 MHz) δ 9.10 (s, 1H), 8.39 (d, J=1.6 Hz, 1H), 8.21-8.12 (m, 2H), 8.05 (s, 1H), 5.27-5.20 (m, 1H), 1.53 (d, J=6.4 Hz, 6H). MS (ESI, m/z): 296.2 $[M+H]^+$.

Example 9: Synthesis of 2-(3-cyano-1-cyclopropyl methyl-1H-indole-5-yl)-2H-1,2,3-triazole-4-formic acid (41)

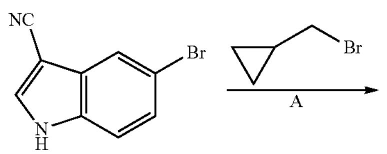

-continued

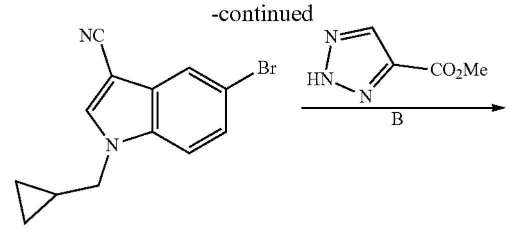

39

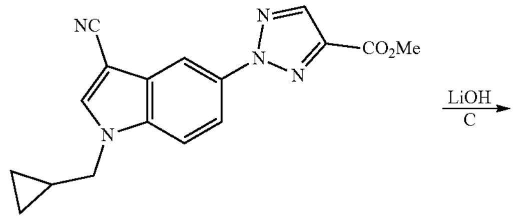

40

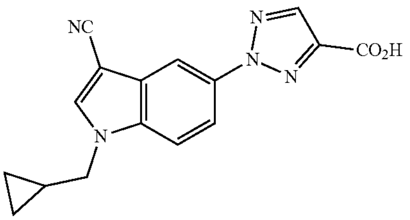

41

Step A: a mixture containing 5-bromo-1H-indole-3-methyl nitrile (1.0 g, 4.52 mmol), cyclopropyl bromomethane (1.83 g, 13.57 mmol), cesium carbonate (4.42 g, 13.57 mmol) and acetonitrile (10 mL) was stirred at 80° C. for 4 hours. After cooling to room temperature, filtering, the cake was washed with ethyl acetate. The solvents were evaporated under reduced pressure and the product was purified by column chromatography (200~300 mesh silica gel, elution with ethyl acetate:petroleum ether=1:4) to give 5-bromo-1-cyclopropyl methyl-1H-indole-3-methyl nitrile (39) (1.18 g). The yield was 94.9%.

Step B: potassium phosphate (2.18 g, 10.25 mmol), bis(dibenzylideneacetone)palladium (295 mg, 0.512 mmol) and 2-di-tert-butylphosphino-3,4,5,6-tetramethyl-2',4',6'-triisopropyl biphenyl (493 mg, 1.02 mmol) were added to a solution of compound 39 (940 mg, 3.42 mmol) and methyl 1,2,3-triazole-4-formate (1.30 g, 10.3 mmol) in toluene (25 mL). After addition, the resulting mixture was stirred overnight under nitrogen at 115° C. After adding ethyl acetate (100 mL) and filtering, the filtrate was washed with saturated salt water (30 mL), and dried over anhydrous sodium sulfate. The solvents were evaporated under reduced pressure and the product was purified by column chromatography (200~300 mesh silica gel, elution with ethyl acetate: petroleum ether=2:7) to give methyl 2-(3-cyano-1-cyclopropyl methyl-1H-indole-5-yl)-2H-1,2,3-triazole-4-formate (40) (211 mg). The yield was 19.2%.

Step C: a mixture containing compound 40 (50 mg, 0.155 mmol), hydrated lithium hydroxide (26.1 mg, 0.622 mmol), water (1 mL), and THF (4 mL) was stirred at room temperature overnight. After adding water (10 mL) and adjusting pH to 1~2 with 1 M hydrochloric acid, the mixture was extracted with ethyl acetate (20 mL×3) and dried over anhydrous sodium sulfate. The solvents were evaporated under reduced pressure and the product was purified by preparative HPLC to give 2-(3-cyano-1-cyclopropyl methyl- 1H-indole-5-1)-2H-1,2,3-triazole-4-formic acid (41). $^1$H NMR (DMSO-$d_6$, 400 MHz) δ 8.54 (s, 1H), 8.52 (s, 1H), 8.24 (d, J=2.0 Hz, 1H), 8.08-7.98 (m, 2H), 4.20 (d, J=7.2 Hz, 2H), 1.37-1.32 (m, 1H), 0.59-0.55 (m, 2H), 0.48-0.45 (m, 2H). MS (ESI, m/z): 307.9 $[M+H]^+$.

Example 10: Synthesis of 2-[3-cyano-1-(tetrahydrofuran-3-yl)-1H-indole-5-yl]-2H-1,2,3-triazole-4-formic acid (44)

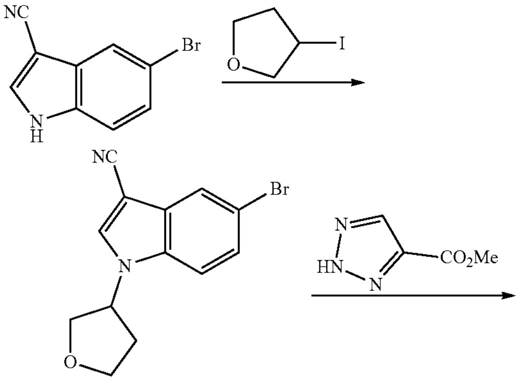

42

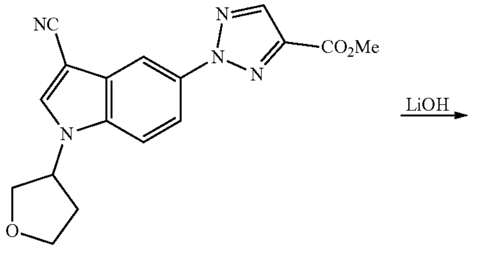

43

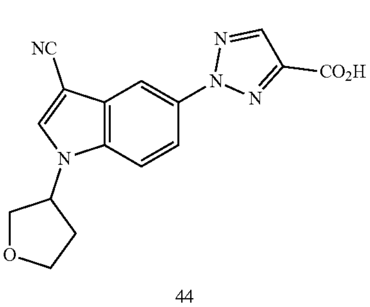

44

The experimental operations for the synthesis of compound 44 were referred to those in Example 9, wherein cyclopropyl bromomethane in step A of Example 9 was replaced by 3-iodotetrahydrofuran. $^1$H NMR (DMSO-$d_6$, 400 MHz) δ 8.53 (s, 1H), 8.48 (s, 1H), 8.24 (d, J=2.0 Hz, 1H), 8.09-8.00 (m, 2H), 5.44-5.40 (m, 1H), 4.20-4.12 (m, 1H), 3.99-3.98 (m, 2H), 3.87-3.83 (m, 1H), 2.58-2.54 (m, 1H), 2.22-2.21 (m, 1H). MS (ESI, m/z): 323.9 $[M+H]^+$.

Example 11: Synthesis of 2-(3-cyano-1-cyclobutyl-1H-indole-5-yl)-2H-1,2,3-triazole-4-formic acid (47)

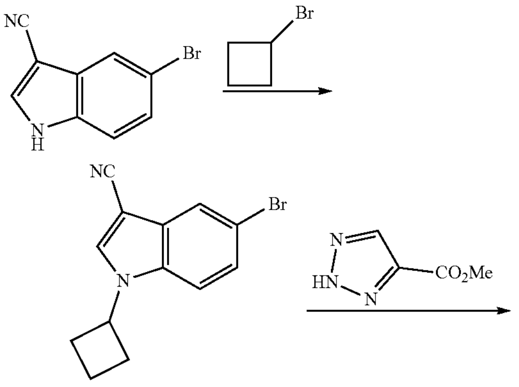

45

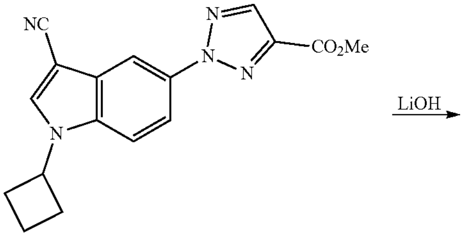

46

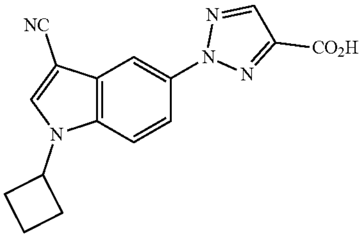

47

The experimental operations for the synthesis of compound 47 were referred to those in Example 9, wherein cyclopropyl bromomethane in step A of Example 9 was replaced by bromocyclobutane. $^1$H NMR (DMSO-$d_6$, 400 MHz) δ 8.69 (s, 1H), 8.51 (s, 1H), 8.22 (s, 1H), 8.04 (dd, J=2.0, 8.8 Hz, 1H), 7.91 (d, J=8.8 Hz, 1H), 5.15-5.11 (m, 1H), 2.55-2.52 (m, 2H), 2.49-2.48 (m, 2H), 1.91-1.86 (m, 2H). MS (ESI, m/z): 308.0 $[M+H]^+$.

Example 12: Synthesis of 1-(3-cyano-1-cyclopropyl-1H-indazole-5-yl)-1H-pyrazole-4-formic acid (50)

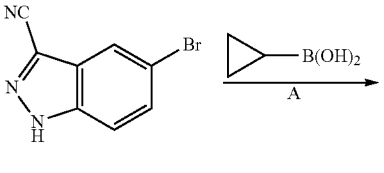

-continued

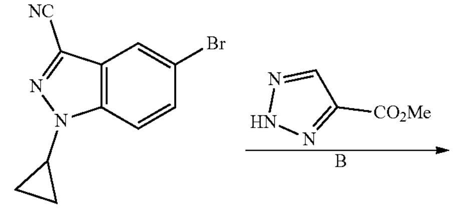

48

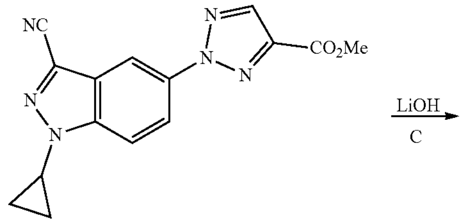

49

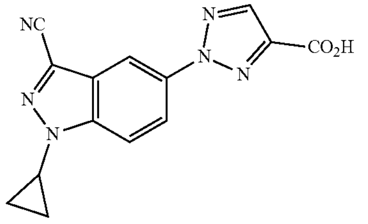

50

Step A: a mixture of compound 5-bromo-1H-indazole-3-methyl nitrile (2.0 g, 9.01 mmol), cyclopropyl boric acid (1.55 g, 18.0 mmol), copper acetate (1.64 g, 9.01 mmol), potassium tert-butanol (1.01 g, 9.01 mmol), DMAP (3.30 g, 27.0 mmol) and toluene (400 mL) was stirred overnight under nitrogen at 95° C. After cooling to room temperature, ethyl acetate (400 mL) was added, and insolubles was filtered through Celite. The filtrate was washed with saturated salt water (100 mL×2) and dried over anhydrous sodium sulfate. The solvents were evaporated under reduced pressure and the product was purified by column chromatography (200~300 mesh silica gel, elution with ethyl acetate:petroleum ether=1:7) to give 5-bromo-1-cyclopropyl-1H-indazole-3-methyl nitrile (48) (630 mg). The yield was 26.7%.

Step B: a mixture containing ethyl 1H-pyrazole-4-formate (53.5 mg, 0.382 mmol) and compound 48 (100 mg, 0.382 mmol), potassium carbonate (105 mg, 0.763 mmol), cuprous iodide (72.7 mg, 0.382 mmol), N,N'-dimethylethylenediamine (33.6 mg, 0.382 mmol) and DMF (2 mL) was stirred under nitrogen at 110° C. for 3 hours. After cooling to room temperature, adding water (20 mL), and extracting with ethyl acetate (30 mL×2), the combined organic phase was washed with saturated salt water (20 mL×2), and dried over anhydrous sodium sulfate. The solvents were evaporated under reduced pressure and the product was purified by column chromatography (200~300 mesh silica gel, elution with ethyl acetate:petroleum ether=1:4) to give ethyl 1-(3-cyano-1-cyclopropyl-1H-indazole-5-yl)-1H-pyrazole-4-formate (49) (100 mg). The yield was 81.5%.

Step C: a mixture containing compound 49 (100 mg, 0.311 mmol), hydrated lithium hydroxide (26.1 mg, 0.622 mmol), water (0.5 mL), and THF (2 mL) was stirred at room temperature overnight. After adding water (10 mL), adjusting the pH value to 3~4 with 1 M hydrochloric acid, the mixture was extracted with ethyl acetate (10 mL×3), and dried over anhydrous sodium sulfate. The solvent was evaporated under reduced pressure and the product was purified by preparative HPLC to give 1-(3-cyano-1-cyclopropyl-1H-indazole-5-yl)-1H-pyrazole-4-formic acid (50). 1H NMR (DMSO-d6, 400 MHz) δ 12.68 (s, 1H), 9.23 (s, 1H), 8.45 (t, J=0.8 Hz, 1H), 8.26-8.23 (m, 1H), 8.11-8.09 (m, 2H), 4.10 (t, J=5.2 Hz, 1H), 1.24-1.22 (m, 4H). MS (ESI, m/z): 293.9 [M+H]+.

Example 13: Synthesis of 1-(7-fluoro-3-iodo-1-isopropyl-1H-indazole-5-yl)-1H-pyrazole-4-formic acid (54)

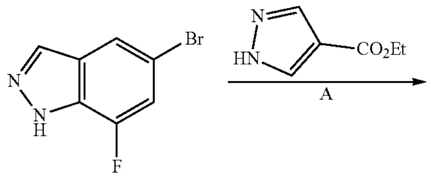

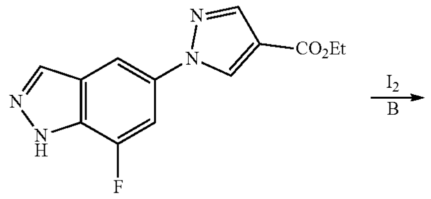

51

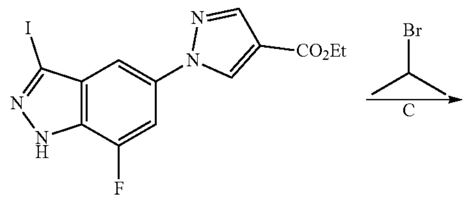

52

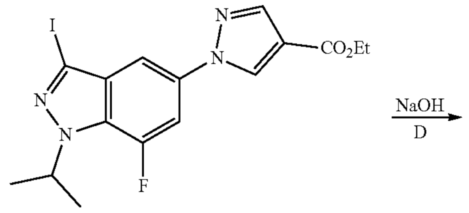

53

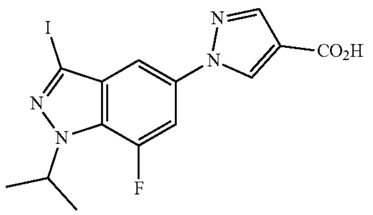

54

Step A: a mixture containing ethyl 1H-pyrazole-4-formate (1.30 g, 9.30 mmol), 5-bromo-7-fluoro-1H-indazole (2.0 g, 9.30 mmol), potassium carbonate (2.57 g, 18.6 mmol), cuprous iodide (1.77 g, 9.30 mmol), N,N'-dimethylethylenediamine (820 mg, 9.30 mmol) and DMF (40 mL) was stirred under nitrogen at 110° C. for 3 hours. After cooling to room temperature, adding water (120 mL), and extracting with ethyl acetate (50 mL×2), the combined organic phase was washed with water (50 mL) and saturated salt water (50 mL), and dried over anhydrous sodium sulfate. The solvent was evaporated under reduced pressure and the product was purified by column chromatography (200~300 mesh silica gel, elution with ethyl acetate:petroleum ether=1:30~5:1) to give ethyl 1-(7-fluoro-1H-indazole-5-yl)-1H-pyrazole-4-formate (51) (2.10 g). The yield was 82.3%.

Step B: potassium carbonate (4.23 g, 30.6 mmol) and iodine (3.89 g, 15.3 mmol) were added to a solution of compound 51 (2.10 g, 7.66 mmol) in DMF (40 mL) under an ice water bath, and the resulting mixture was stirred overnight at room temperature. After adding water (120 mL) and extracting with ethyl acetate (150 mL×2), the combined organic phase was washed with water (100 mL) and saturated salt water (100 mL), and dried over anhydrous sodium sulfate. The solvent was evaporated under reduced pressure and the product was purified by column chromatography (200~300 mesh silica gel, elution with ethyl acetate:petroleum ether=1:5~5:1) to give ethyl 1-(7-fluoro-3-iodo-1H-indazole-5-yl)-1H-pyrazole-4-formate (52) (1.0 g). The yield was 32.6%.

Step C: a mixture containing compounds 52 (790 mg, 1.97 mmol), isopropane bromide (720 mg, 5.85 mmol), cesium carbonate (1.92 g, 5.89 mmol), and acetonitrile (14 mL) was stirred overnight at 60° C. After cooling to room temperature and filtering to remove insolubles, the solvents were evaporated under reduced pressure and the product was purified by column chromatography (200~300 mesh silica gel, elution with ethyl acetate:petroleum ether=1:20~1:3) to give ethyl 1-(7-fluoro-3-iodo-1-isopropyl-1H-indazole-5-1)-1H-pyrazole-4-formate (53) (550 mg). The yield was 69.8%.

Step D: a mixture containing compound 53 (220 mg, 0.497 mmol), 2 M sodium hydroxide solution (4 mL), and THF (1 mL) was stirred at 50° C. for 0.5 hour. After adding water (15 mL), and extracting with dichloromethane (10 mL×2), the product was in the aqueous phase. The pH value was adjusted to 2~3 with 2 M hydrochloric acid in the aqueous phase, and the filter cake was recrystallized with ethyl acetate/petroleum ether after filtering to give 1-(7-fluoro-3-iodo-1-isopropyl-1H-indazole-5-yl)-1H-pyrazole-4-formic acid (54). $^1$H NMR (DMSO-$d_6$, 400 MHz) δ 9.21 (s, 1H), 8.13 (s, 1H), 8.09 (d, J=1.6 Hz, 0.5H), 8.06 (d, J=1.6 Hz, 0.5H), 7.84 (d, J=1.6 Hz, 1H), 5.11-5.05 (m, 1H), 1.54 (d, J=6.4 Hz, 6H). MS (ESI, m/z): 414.9 $[M+H]^+$.

Example 14: Synthesis of 1-(3-cyano-7-fluoro-1-isopropyl-1H-indazole-5-yl)-1H-pyrazole-4-formic acid (55)

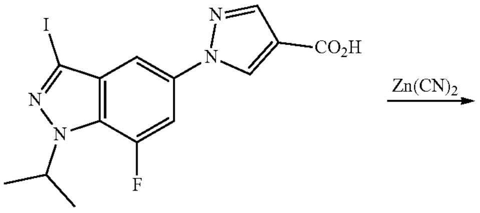

54

-continued

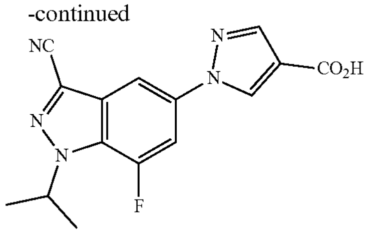

55

Using compound 54 as raw material, the experimental operations for the synthesis of compound 55 were referred to those in Step G of Example 4. $^1$H NMR (DMSO-$d_6$, 400 MHz) δ 9.28 (s, 1H), 8.34 (d, J=1.6 Hz, 1H), 8.17-8.14 (m, 2H), 5.24-5.19 (m, 1H), 1.59 (d, J=6.4 Hz, 6H). MS (ESI, m/z): 314.1 $[M+H]^+$.

Example 15: Synthesis of 2-(3-cyano-1-isopropyl-1H-indazole-5-yl) isonicotinic acid (57)

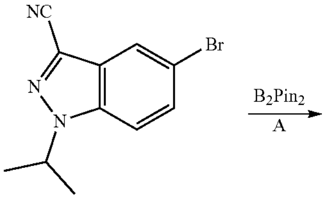

25

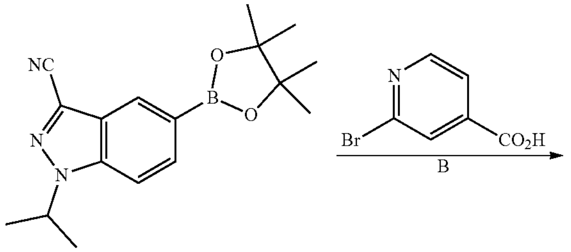

56

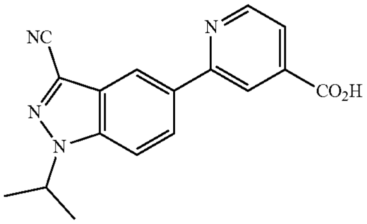

57

Step A: a mixture of compound 25 (500 mg, 1.89 mmol), bis(pinacolato)diboron (721 mg, 2.84 mmol), potassium acetate (557 mg, 5.68 mmol) and 1,1'-bis(diphenylphosphino)ferrocene]dichloropalladium (139 mg, 0.190 mmol) and dioxane (10 mL) was stirred overnight at 80° C. After cooling to room temperature and filtering, the cake was washed with ethyl acetate. The solvents were evaporated under reduced pressure and the the product was purified by column chromatography (200~300 mesh silica gel, elution with ethyl acetate:petroleum ether=1:10) to give 1-isopropyl-5-(4,4,5,5-tetramethyl-1,3,2-dioxaborolan-2-yl)-1H-indazole-3-methyl nitrile (56) (360 mg). The yield was 61.2%.

Step B: a mixture containing compound 56 (200 mg, 0.642 mmol), 2-bromopyridine-4-formic acid (130 mg, 0.643 mmol), potassium carbonate (178 mg, 1.29 mmol), dioxane (2.5 mL) and water (0.5 mL) was added to 1,1'-bis(diphenylphosphino)ferrocene]dichloropalladium (52 mg, 0.064 mmol). After addition, the resulting mixture was stirred under nitrogen at 85° C. for 2 hours. After cooling to room temperature, adding water (50 mL), and extracting with ethyl acetate (30 mL×2), the product was in the aqueous phase. In the aqueous phase, the pH value was adjusted to 3~4 with 1 M hydrochloric acid, then the aqueous phase was extracted with ethyl acetate (30 mL×2), and dried over anhydrous sodium sulfate. The solvent was evaporated under reduced pressure and the product was purified by preparative HPLC to give 2-(3-cyano-1-isopropyl-1H-indazole-5-yl) isonicotinic acid (57). $^1$H NMR (DMSO-$d_6$, 400 MHz) δ 8.88 (d, J=4.8 Hz, 1H), 8.65 (s, 1H), 8.50 (s, 1H), 8.40 (dd, J=1.6, 9.2 Hz, 1H), 8.13 (d, J=8.8 Hz, 1H), 7.82 (d, J=8.8 Hz, 1H), 5.30-5.23 (m, 1H), 1.58 (d, J=6.8 Hz, 6H). MS (ESI, m/z): 307.3 $[M+H]^+$.

Example 16: Xanthine Oxidase Activity Inhibition Test

I. Principle

A double enzyme coupling reaction of Xanthine Oxidase (XO) and Horseradish Peroxidase (HRP) and their substrates was used to test the activity inhibition of xanthine oxidase. First, xanthine oxidase oxidized hypoxanthine to produce xanthine and hydrogen peroxide, and further oxidized xanthine to produce uric acid and hydrogen peroxide. Then horseradish peroxidase catalyzed a reaction of hydrogen peroxide with 10-acetyl-3,7-dihydroxyphenoxazine (Ampliflu Red) to produce Resorufin, a strong fluorescent compound. The fluorescence intensity of resorufin was determined by fluorescence enzyme spectrometer in direct proportion to xanthine oxidase activity.

II. Test Reagents and Equipment

Febuxostat was purchased from Beijing Lianben Pharmchemicals Tech. Co., Ltd.; XO, Ampliflu Red and hypoxanthine were purchased from Sigma-Aldrich Co., LLC; HRP was purchased from Shanghai Yuanye Bio-technology Co., Ltd.; 96-well polypropylene reaction plate was purchased from Greiner Bio One; DMSO was purchased from Sinopharm Chemical Reagent Co., Ltd.

Vitor X4 microplate reader was purchased from Perkin Elmer, Inc.

III. Preparation of Test Compounds and Reaction Solutions

A certain amount of test compounds 15, 24, 28, 32, 35, 38, 41, 44, 47, 50, 57 and the control compound Febuxostat were dissolved in DMSO (the product of Sinopharm Chemical Reagent Co., Ltd). In 96-well polypropylene reaction plate, the test compound was diluted into a 200-fold concentration of solution with DMSO through 2.5-fold serial dilution, and further diluted in ultra-pure water to obtain a series of 3-fold concentration of diluted solution.

Reaction solution A: 6 mU/mL xanthine oxidase solution was prepared in 0.1M Tris-HCl (pH7.5) buffer solution.

Reaction solution B: a mixture of 0.6 U/mL horseradish peroxidase solution, 0.15 mM Ampliflu Red and 0.3 mM hypoxanthine in 0.1M Tris-HCl (pH 7.5) buffer solution. The solution was protected from light at 4° C. and was prepared when it was ready for use.

4. Test Methods and Results

9 μL reaction solution A was mixed with 3-fold concentration serial dilution solution of 9 μL test compound in a 96-well test plate, placed on a flat plate oscillator, and mixed at 30° C. at 100 rpm for 30 min. Then 9 μL reaction solution B was added. The enzyme reaction was carried out at 30° C. for 30 minutes. The fluorescence intensity at excitation light 530 nm and emission light 590 nm was measured by a microplate reader. The fluorescence intensity of the control without xanthine oxidase was 0%, and that of the control without the test compound was 100%. The 50% inhibition concentration ($IC_{50}$) of the test compound and the control compound was calculated using the software Graph Pad Prism 5.

The test results were shown in Table 1. It can be seen from the results in Table 1 that the compounds provided by the invention exhibited excellent xanthine oxidase inhibition in vitro pharmacological tests.

TABLE 1

Xanthine oxidase inhibitor activity $IC_{50}$ of each compound

| Compound No. | $IC_{50}$(nM) |
|---|---|
| 15 | 1.84 |
| 24 | 3.65 |
| 28 | 7.91 |
| 32 | 5.11 |
| 35 | 11.83 |
| 38 | 3.24 |
| 41 | 1.72 |
| 44 | 9.58 |
| 47 | 1.71 |
| 50 | 9.89 |
| 57 | 2.89 |
| Febuxostat | 2.96 |

Example 17: Experimental Study of Compound in the Treatment of Hyperuricemia in Rats I. Experimental Materials 1. Test Drug Compounds 15, 24 and 38 were white powder, and compound 57 was light yellow powder, which was ground with 0.5% CMC-Na before use and prepared into suspension with corresponding concentrations (0.2 and 0.4 mg/mL) for gavage.

Febuxostat, purchased from Sigma, was ground with 0.5% CMC-Na before use and prepared into suspension with corresponding concentrations (0.2 and 0.4 mg/mL) for gavage.

2. Animals and Feeding 2.1 Species and Origin of Animals

SD rat, SPF grade, male, weighing 180-220 g, purchased from Shanghai Slake Experimental Animal Co., Ltd., production license number: SCXK (Hu) 2017-0005, quality certificate number: 20170005050604.

2.2 Feeding Conditions

The rats were all fed in an independent air supply cage with 10000 level of air cleanliness and a laboratory temperature of 26±2° C. Relative humidity 60%~80%; Frequency of air exchange per hour: 10-15 times/hour; Light cycle: 12 (day)/12 (night) hours, 3 animals per cage.

Feed: Full-priced rat pellet feed, purchased from Jiangsu Synergetic Pharmaceutical Bioengineering Co., Ltd., its quality conformed to GB14924.1-2001 "Laboratory animals—General quality standard for formula feeds".

Packing material: Sterilized granule packing material, purchased from Jiangsu Synergetic Pharmaceutical Bioengineering Co., Ltd.

Drinking water: Drinking purified water and drinking freely after acidification.

3. Main Instruments and Equipment

Varioskan LUX multi-function microplate reader purchased from Thermo, USA; BS210S precision electronic balance (0.1 mg~10 g) purchased from Sartorius, Germany; FEJ-200 electronic balance (0.1~200 g) purchased from Fuzhou Furi Weighing Electronics Co., Ltd. Pacific TII+ Genpure XCAD PLUS UV/TOC/UF Pure Water Ultrapure water system purchased from Thermo, USA.

4. Main Reagents

Uric acid assay kit (phosphotungstic acid reduction method), lot No.: 20210515, purchased from Nanjing Jiancheng Biological Engineering Research Institute; Potassium oxonate, item No. O0164, lot No. T6GKM-TA, purchased from Tokyo Chemical Industry (TCI), Japan; Sodium carboxymethyl cellulose (CMC-Na), lot No. 20170810, chemical pure, purchased from Sinopharm Chemical Reagent Co., Ltd.

II. Experimental Methods

1. Group Assignment

72 SD rats, male, weighed about 200-230 g after one week of acclimatization. The SD rats were randomly divided into 10 groups according to body weight, with 6 animals in each group: (1) vehicle group (0.5% CMC-Na), (2) model group (0.5% CMC-Na), (3) Febuxostat 1 mg/kg, (4) Febuxostat 2 mg/kg, (5) compound 15, 1 mg/kg, (6) compound 15, 2 mg/kg, (7) compound 24, 1 mg/kg, (8) compound 24, 2 mg/kg, (9) compound 38, 1 mg/kg, (10) compound 38, 2 mg/kg, (11) compound 57, 1 mg/kg, (12) compound 57, 2 mg/kg. Drugs for each group were prepared into suspension with corresponding concentration, and the administration volume was 0.5 mL/100 g.

2. Model Establishment, Administration Scheme and Detection Index

After purchased and fed for acclimatization, the rats in each group were fasted for 12 h, and the the model was established by intraperitoneal injection with potassium oxonate at the dose of 300 mg/kg, and each of the test drug groups were administrated once by gavage after model establishment. Blood samples were collected from posterior orbital venous plexus before and 1, 3 and 5 h after potassium oxonate injection, centrifugated at 3500 rpm for 10 min, and 30 μL serum was taken to determine uric acid levels at each time point.

Then in two consecutive days, rat models were established with potassium oxonate by intraperitoneal injection at a dose of 300 mg/kg every day, and each test drug group was administrated once by gavage after model establishment. On the third day of administration, the rats were fasted for 12 h, and with the same test method on the first day, blood samples were collected from the posterior orbital venous plexus before and 1, 3 and 5 h after potassium oxonate injection, centrifuged at 3500 rpm for 10 min, and 30 μL serum was taken to determine the uric acid level at each time point.

3. Data Processing and Statistical Methods

The measurement data of each experiment were expressed as (mean)±s (standard deviation). ANOVA-Dunnett T test was used to investigate the significance between groups, and P<0.05 was used as a significant index, P<0.01 was used as a very significant index.

III. Experimental Results

1. Effect of 1-Day Administration on Serum Uric Acid Level in Rats

Compared with the vehicle group, the serum uric acid level in the model group was significantly increased at 1, 3 and 5 h after modeling (P<0.01). Compared with the model group at the same time point, 1 mg/kg and 2 mg/kg groups of Febuxostat significantly decreased the serum uric acid level at 1, 3 and 5 h after model establishment (P<0.01). Compared with model group, 2 mg/kg group of compound 15 significantly decreased serum uric acid level at 1 h after model establishment (P<0.01), both 1 and 2 mg/kg groups of compound 24 significantly decreased serum uric acid level at 1 h after model establishment (P<0.01), 1 and 2 mg/kg groups of compound 38 significantly decreased serum uric acid levels at 1, 3 and 5 h after model establishment (P<0.01), 1 and 2 mg/kg groups of compound 57 significantly decreased serum uric acid levels at 1, 3 and 5 h after model establishment (P<0.01 or P<0.05). The results were shown in Table 2.

TABLE 2

Effect of 1-day administration on serum uric acid level in rats with hyperuricemia induced by potassium oxonate ($\bar{x} \pm s$)

| Group | Dose (mg/kg) | Number of animals | Uric acid (μmol/L) 0 h | 1 h | 3 h | 5 h |
|---|---|---|---|---|---|---|
| vehicle group | — | 6 | 77.3 ± 5.0 | 83.1 ± 3.6 | 77.7 ± 11.4 | 91.0 ± 3.9 |
| model group | — | 6 | 65.1 ± 4.1 | 122.7 ± 15.4## | 140.0 ± 13.8## | 112.6 ± 13.5## |
| Febuxostat | 1 | 6 | 81.3 ± 7.8 | 76.4 ± 11.4** | 91.3 ± 13.3* | 65.7 ± 12.4** |
| | 2 | 6 | 67.2 ± 1.9 | 59.7 ± 6.6** | 60.7 ± 15.0* | 52.4 ± 6.6** |
| compound 15 | 1 | 6 | 72.0 ± 6.7 | 104.3 ± 20.3 | 121.6 ± 12.2 | 118.4 ± 15.3 |
| | 2 | 6 | 74.1 ± 10.3 | 98.1 ± 6.3** | 130.7 ± 11.5 | 109.7 ± 22.5 |
| compound 24 | 1 | 6 | 65.3 ± 5.8 | 96.2 ± 9.3** | 131.0 ± 18.9 | 96.8 ± 13.6 |
| | 2 | 6 | 77.6 ± 9.2 | 96.8 ± 5.4** | 126.4 ± 14.4 | 105.1 ± 16.6 |
| compound 38 | 1 | 6 | 75.6 ± 6.8 | 70.6 ± 7.7** | 74.6 ± 19.6* | 64.3 ± 10.6** |
| | 2 | 6 | 73.1 ± 6.7 | 66.5 ± 7.5** | 77.4 ± 9.2** | 56.8 ± 4.0** |
| compound 57 | 1 | 6 | 71.2 ± 8.3 | 74.7 ± 11.3* | 99.5 ± 12.4* | 85.7 ± 8.5** |
| | 2 | 6 | 74.5 ± 8.9 | 64.0 ± 13.5** | 107.4 ± 12.5 | 94.8 ± 6.4* |

Note:

P < 0.01, compared with the vehicle group at the same time point;

**P < 0.01, compared with the model group at the same time point.

2. Effect of 3-Day of Administration on Serum Uric Acid Level in Rats

Compared with vehicle group, serum uric acid level in potassium oxonate model group was significantly increased at 1 and 3 h after model establishment (P<0.01). Compared with the model group at the same time point, 1 and 2 mg/kg groups of Febuxostat significantly decreased the serum uric acid level at 1, 3 and 5 h after model establishment (P<0.05 or P<0.01). Compared with model group, 2 mg/kg group of compound 24 significantly decreased serum uric acid level at 3 h after model establishment (P<0.01), 1 and 2 mg/kg groups of compound 38 significantly decreased serum uric acid levels at 1, 3 and 5 h after model establishment (P<0.01), 1 and 2 mg/kg groups of compound 57 significantly decreased serum uric acid levels at 1 and 3 h after model establishment (P<0.01). The results were shown in Table 3.

TABLE 3

Effect of 3-day of administration on serum uric acid level in rats with hyperuricemia induced by potassium oxonate ( $\bar{x} \pm s$)

| Group | Dose (mg/kg) | Number of animals | Uric acid (μmol/L) 0 h | 1 h | 3 h | 5 h |
|---|---|---|---|---|---|---|
| vehicle group | — | 6 | 77.3 ± 5.0 | 83.1 ± 3.6 | 77.7 ± 11.4 | 91.0 ± 3.9 |
| model group | — | 6 | 65.1 ± 4.1 | 122.7 ± 15.4## | 140.0 ± 13.8## | 112.6 ± 13.5## |
| Febuxostat | 1 | 6 | 66.0 ± 11.3 | 53.0 ± 12.0** | 71.4 ± 23.5** | 61.1 ± 8.1* |
| | 2 | 6 | 65.5 ± 8.8 | 47.5 ± 7.9** | 51.8 ± 6.7** | 49.2 ± 2.4** |
| compound 15 | 1 | 6 | 70.9 ± 12.8 | 78.4 ± 12.1 | 166.1 ± 37.5 | 100.0 ± 12.5 |
| | 2 | 6 | 64.1 ± 4.8 | 88.2 ± 21.3 | 139.8 ± 32.7 | 97.6 ± 21.0 |
| compound 24 | 1 | 6 | 87.8 ± 16.2 | 105.5 ± 12.7 | 155.3 ± 38.2 | 102.6 ± 8.3 |
| | 2 | 6 | 90.4 ± 9.1 | 97.2 ± 27.5 | 104.0 ± 5.8** | 97.0 ± 14.6 |
| compound 38 | 1 | 6 | 61.0 ± 5.7 | 62.1 ± 14.1** | 69.4 ± 16.1** | 55.1 ± 5.8** |
| | 2 | 6 | 60.9 ± 8.1 | 54.4 ± 5.1** | 73.1 ± 9.4** | 58.1 ± 9.6** |
| compound 57 | 1 | 6 | 70.8 ± 8.6 | 57.5 ± 9.3** | 75.3 ± 6.3** | 90.0 ± 5.9 |
| | 2 | 6 | 72.7 ± 15.6 | 63.6 ± 11.7** | 75.2 ± 16.9** | 81.1 ± 8.0 |

Note:
P < 0.01, compared with the vehicle group at the same time point;
**P < 0.01, compared with the model group at the same time point.

What is claimed is:

1. A compound in general formula (I) or a pharmaceutically acceptable salt thereof, (I)

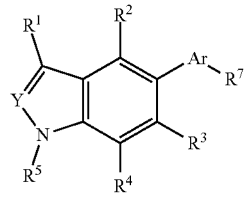

wherein,

Y is N or C—$R^6$;

$R^1$ is cyano;

$R^2$, $R^3$, or $R^4$ is hydrogen;

$R^5$ is $C_{1-6}$ alkyl, substituted $C_{1-6}$ alkyl, $C_{3-6}$ cycloalkyl, substituted $C_{3-6}$ cycloalkyl, $C_{3-6}$ heterocycloalkyl or substituted $C_{3-6}$ heterocycloalkyl, the substituents of each group involved in $R^5$ are selected from one or more of the group consisting of deuterium, cyano, nitro, halogen, $C_{1-6}$ alkyl, $C_{1-6}$ alkoxy, $C_{3-6}$ cycloalkyl and $C_{3-6}$ heterocycloalkyl;

$R^6$ is hydrogen;

Ar is a non-substituted or substituted for the following groups:

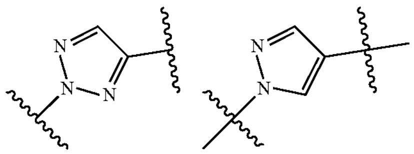

-continued

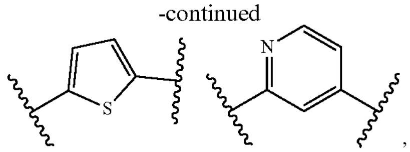

, wherein the substituents of the groups involved in Ar are selected from one or more of the group consisting of the deuterium, halogen, and $C_{1-3}$ alkyl; and when Y is C—$R^6$, Ar is only a non-substituted or substituted

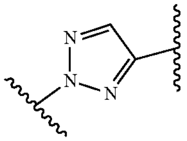 [SMILES: *c1cnn(*)n1]

$R^7$ is a carboxyl or $C_{2-6}$ ester group.

2. The compound or pharmaceutically acceptable salt thereof according to claim 1, where $R^5$ is $C_{3-6}$ alkyl, substituted $C_{1-6}$ alkyl, $C_{3-6}$ cycloalkyl, substituted $C_{3-6}$ cycloalkyl, $C_{3-6}$ heterocycloalkyl or substituted $C_{3-6}$ heterocycloalkyl; the substituents of the groups involved in $R^5$ are selected from one or more of the group consisting of deuterium, cyano, nitro, halogen, $C_{1-5}$ alkyl, $C_{1-5}$ alkoxy and $C_{3-6}$ cycloalkyl.

3. The compound or pharmaceutically acceptable salt thereof according to in claim 1, wherein $R^5$ is $C_{3-6}$ alkyl, substituted $C_{1-6}$ alkyl, $C_{3-6}$ cycloalkyl, substituted $C_{3-6}$ cycloalkyl, tetrahydrofuran, substituted tetrahydrofuran, tetrahydrothiophene, substituted tetrahydrothiophene, tetrahydropyrrole or substituted tetrahydropyrrole; the substituents of the groups involved in $R^5$ are selected from one or more of the group consisting of deuterium, cyano, nitro, halogen, $C_{1-5}$ alkyl, $C_{1-5}$ alkoxy and $C_{3-6}$ cycloalkyl.

4. The compound or the pharmaceutically acceptable salt thereof according to claim 1, wherein $R^7$ is a carboxyl group.

5. The compound or the pharmaceutically acceptable salt thereof according to claim 1, wherein the compound is selected from the group consisting of the following:

7

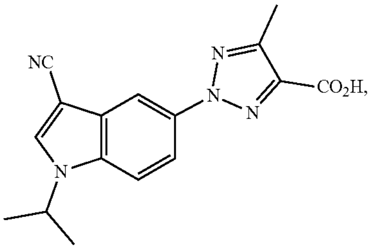

14

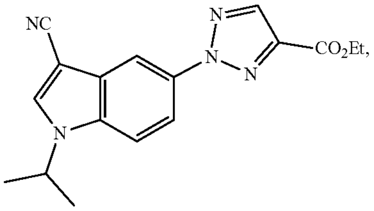

15

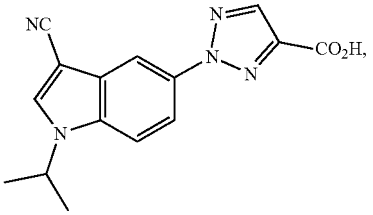

24

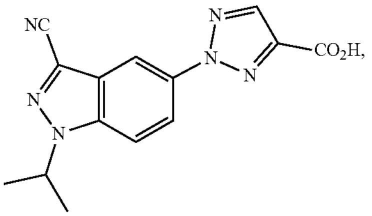

28

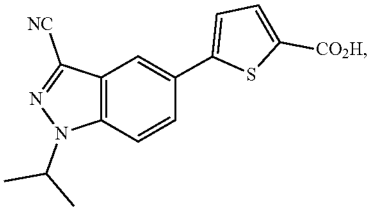

-continued

32

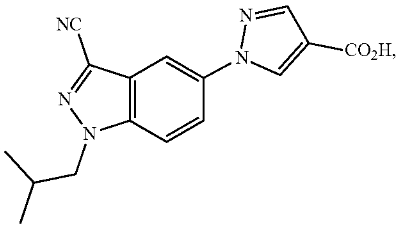

35

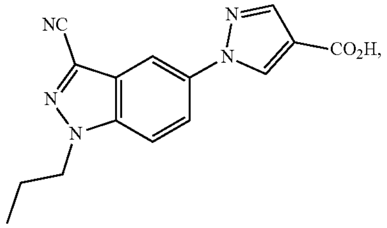

38

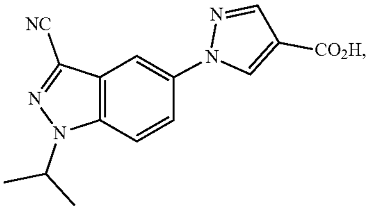

41

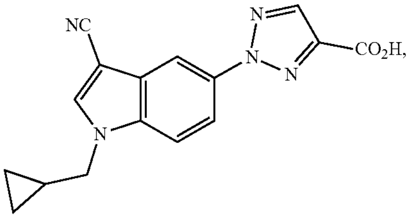

44

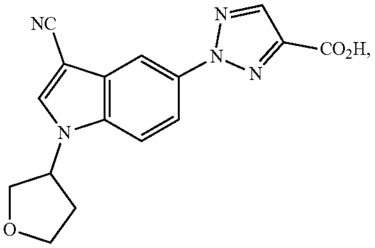

47

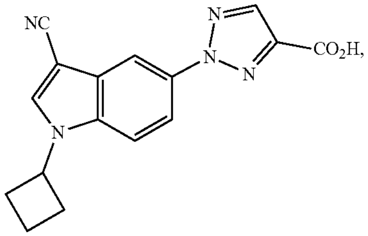

50

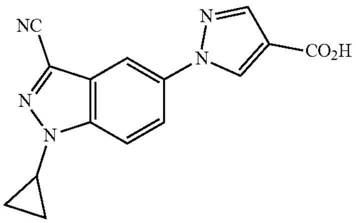

and

-continued

57

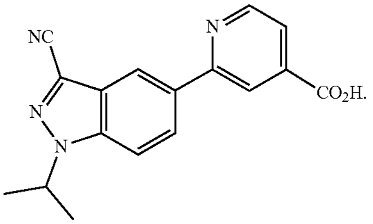

6. A pharmaceutical composition consisting of the compound or pharmaceutically acceptable salt thereof according to claim 1 as the active substance, in combination with pharmaceutically acceptable excipients.

7. A method for treating a disease comprising a step of administering the compound or pharmaceutically acceptable salts thereof according to claim 1 as xanthine oxidase inhibitor drugs to a subject, wherein the disease is a gout or a hyperuricemia.

8. The compound or the pharmaceutically acceptable salt thereof according to claim 1, wherein the compound is prepared as an anti-gout and anti-hyperuricemia drug.

* * * * *